(12) United States Patent
Chu

(10) Patent No.: US 9,579,317 B2
(45) Date of Patent: Feb. 28, 2017

(54) PEPTIDE-DRUG CONJUGATES

(71) Applicant: JiaRui Biopharmaceuticals, Ltd., Yixing (CN)

(72) Inventor: Shaosong Chu, Encinitas, CA (US)

(73) Assignee: Jiarui Biopharmaceuticals, Ltd., Yixing (CN)

( * ) Notice: Subject to any disclaimer, the term of this patent is extended or adjusted under 35 U.S.C. 154(b) by 0 days.

(21) Appl. No.: 14/726,897

(22) Filed: Jun. 1, 2015

(65) Prior Publication Data

US 2015/0343083 A1 Dec. 3, 2015

Related U.S. Application Data

(60) Provisional application No. 62/007,159, filed on Jun. 3, 2014.

(51) Int. Cl.

| | | |
|---|---|---|
| A61K 38/00 | (2006.01) | |
| A61K 47/00 | (2006.01) | |
| A61K 38/14 | (2006.01) | |
| C07K 9/00 | (2006.01) | |
| A61K 38/06 | (2006.01) | |
| C07K 5/00 | (2006.01) | |
| C07K 7/00 | (2006.01) | |
| C07K 16/00 | (2006.01) | |
| C07K 17/00 | (2006.01) | |
| A61K 31/4745 | (2006.01) | |
| A61K 31/407 | (2006.01) | |
| A61K 31/704 | (2006.01) | |
| A61K 47/48 | (2006.01) | |

(52) U.S. Cl.
CPC ........ *A61K 31/4745* (2013.01); *A61K 31/407* (2013.01); *A61K 31/704* (2013.01); *A61K 47/481* (2013.01); *A61K 47/48338* (2013.01)

(58) Field of Classification Search
CPC ................................................ A61K 47/48246
See application file for complete search history.

(56) References Cited

U.S. PATENT DOCUMENTS

| | | | | |
|---|---|---|---|---|
| 3,803,223 | A * | 4/1974 | Mazur et al. ......... | C07C 271/22 426/548 |
| 6,214,345 | B1 | 4/2001 | Firestone et al. | |
| 7,608,591 | B2 | 10/2009 | Liu et al. | |
| 8,314,060 | B2 | 11/2012 | Gengrinovitch | |
| 2009/0175873 | A1* | 7/2009 | Liu ...................... | A61K 31/337 424/139.1 |
| 2011/0300147 | A9 | 12/2011 | Liu | |
| 2014/0057844 | A1 | 2/2014 | Su et al. | |

FOREIGN PATENT DOCUMENTS

| | | | | |
|---|---|---|---|---|
| WO | WO 2004111192 A2 * | 12/2004 | ....... | A61K 47/48246 |
| WO | WO 2007064759 A2 * | 6/2007 | ........... | A61K 31/337 |

OTHER PUBLICATIONS

Bajjuri et al. "The Legumain Protease-Activated Auristatin Prodrugs Suppress Tumor Growth and Metastasis without Toxicity" ChemMedChem 6:54-59. Published Jan. 3, 2011.*
Senter P and Benjamin D "Recent Advancements in the Use of Antibody-Drug Conjugates for Cancer Therapy", p. 325-340, from Emerging Protein Biotherapeutics. Edited by Grewal I. Published 2009.*
Dubowchik et al. "Cathepsin B-Sensitive Dipeptide Prodrugs. 2. Models of Anticancer Drugs Paclitaxel (Taxol), Mitomycin C and Doxorubicin" Bioorgan. Med. Chem. Lett. 8:3347-3352. Published 1998.*
Wu et al., "Targeting Cell-Impermeable Prodrug Activation to Tumor Microenvironment Eradicates Multiple Drug-Resistant Neoplasms" Cancer Research Jan. 2006; 66: (2) 970-980.
Liu et al., "Overexpression of Legumain in Tumors is Significant for Invasion/Metastasis and a Candidate Enzymatic Target for Prodrug Therapy1" Cancer Research Jun. 2003; 63: 2957-2964.
Handbook of Pharmaceutical Salts Properties, Selection and Use, P. Heinrich Stahl and Camille G. Wermuth, Eds., International Union of Pure and Applied Chemistry (IUPAC), Wiley-VCH 2002.
Encyclopedia of Pharmaceutical Technology. Eds. J. Swarbrick and J.C. Boylan, vol. 13, Marcel Dekker, Inc., New York, Basel, Hong Kong 1995, pp. 453-499.
Zhou et al. "Curcumin improves MMC-based chemotherapy by simultaneously sensitising cancer cells to MMC and reducing MMC-associated side-effects" European Journal of Cancer, 47 (2011) pp. 2240-2247.
Han et al. "Studies on the Mechanism of Mitomycin C(1) Electrophilic Transformations: Structure-Reactivity Relationships" J. Org. Chem. 1992, 57, 1799-1807.
Sastry et al. "Solution Structure of the Monoalkylated Mitomycin C-DNA Complex", J. Mol. Biol. (1995) 247, 24338-3597.
International Search Report and Written Opinion in International Application No. PCT/US15/33509, dated Nov. 6, 2015, 11 pages.

* cited by examiner

*Primary Examiner* — Christina Bradley
*Assistant Examiner* — Zachary J Miknis
(74) *Attorney, Agent, or Firm* — Fish & Richardson P.C.

(57) ABSTRACT

Peptide-drug conjugates comprising p-aminobenzyl carbamoyl or p-aminobenzolyl carbonate self-immolating linkers are disclosed. The peptide-drug conjugates comprise a peptide moiety that can be cleaved by cellular proteases, bound to the self-immolating linker, which linker is bound to a cytotoxic drug moiety. Upon cleavage of the peptide moiety, the linker self-immolates, releasing the cytotoxic drug in active form. Dimeric structures of the peptide drug conjugates comprising two molecules of cytotoxic drug per conjugate are also disclosed.

20 Claims, 3 Drawing Sheets

PEPTIDE-DRUG CONJUGATES

RELATED APPLICATION

This application claims benefit of U.S. Provisional Application No. 62/007,159 filed Jun. 3, 2014. The text of which is incorporated by reference in its entirety herewith.

FIELD OF THE INVENTION

The present invention relates to tumor-specific, peptide-drug conjugates and pharmaceutical compositions which include the conjugates. The invention further relates to use of such conjugates and compositions as antitumor agents for the treatment of cancer in mammals, particularly humans.

BACKGROUND AND RELATED ART

Cancerous cells often over-express certain proteases compared to normal cells. This has prompted efforts to target cancerous cells by linking a cytotoxic therapeutic agent to a peptide that a tumor protease cleaves, to release the cytotoxic drug proximate to or within cancerous cells while sparing or less substantially impacting normal cells.

U.S. Pat. No. 6,214,345 discloses tumor-specific peptide-drug conjugates that include a self-immolating linker and are selectively activated at the site of a tumor, wherein the drug may be mitomycin or doxorubicin, and the self-immolating linker is p-aminobenzyl alcohol.

Cells which express asparaginases make attractive targets for the peptide-drug conjugate approach, because many tumors over-express these proteases. One such asparaginase, legumain, has attracted particular attention in this connection (Wu et al., Cancer Research 2006; 66: 970-980; Liu et al., Cancer Research 2003; 63: 2957-2964; Bajjuri et al., ChemMedChem. 2011; 6:.doi: 10.1002/cmdc.201000478; http://www.ncbi.nlm.nih.gov/pmc/articles/PMC3549592/pdf/ni hm 54-59 s-340268.pdf.).

Mitomycin, doxorubicin and camptothecin have attracted attention as drugs employed in peptide-drug conjugate therapies. U.S. Pat. No. 7,608,591; US Published Application 20110300147; US Published Application 20090175873; and U.S. Pat. No. 8,314,060 disclose examples of peptide-drug conjugates that target legumain with drugs that include doxorubicin.

Each of the above references is hereby incorporated by reference in its entirety.

These previous approaches have generally involved chemical modification of the drug moiety, which can adversely affect the drug's efficacy. Coupling of peptides directly (through the C-terminal carboxyl group) to the aziridine N atom of mitomycin yields a secondary amide, a functional group that typically is not subject to attack by proteases. Moreover, studies on mitomycin indicate the role of an NH group in the aziridine ring for biological activity. Thus there is a need for improved conjugates which target anti-tumor drugs such as mitomycin to tumor cells which express legumain and other asparaginases.

SUMMARY OF THE INVENTION

Figure 1:
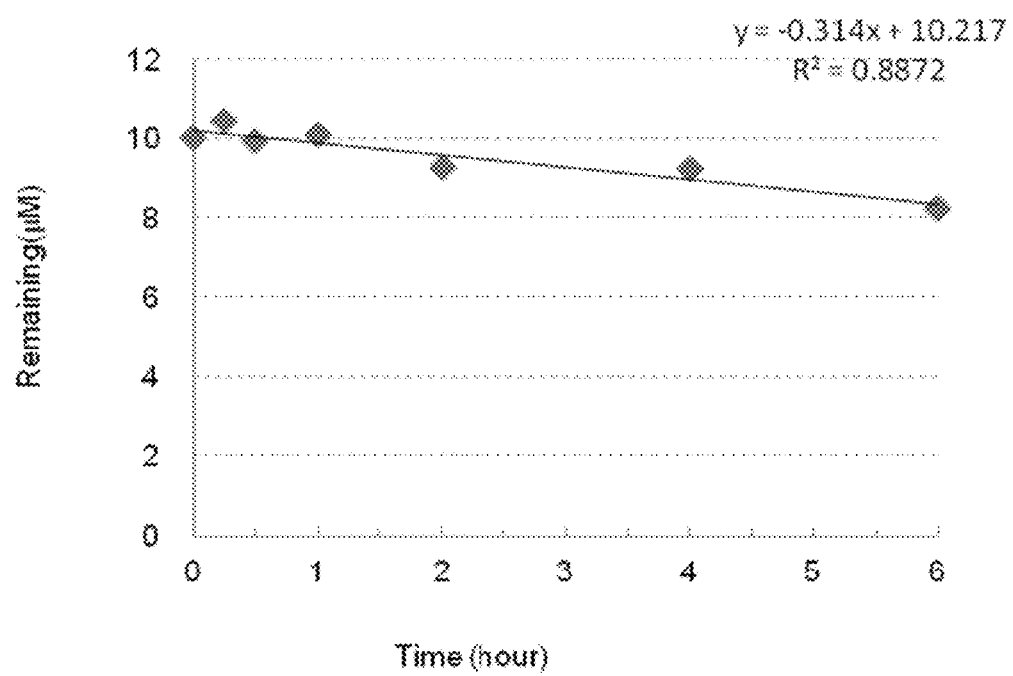
FIG. 1 is a graph showing the rate of decay of $N^\alpha$-succinamic acid-Ala-Ala-Asn-PABC-mitomycin [conjugate 8 herein] as a function of time when exposed to human plasma.

Certain embodiments of the invention are peptide-drug conjugates. Such conjugates comprise, generally: 1) a peptide moiety that can be cleaved by cellular proteases, bound to 2) a self-immolating linker, in particular p-aminobenzyl carbamoyl or p-aminobenzyl carbonate moiety, which is in turn bound to 3) a cytotoxic drug moiety. In these embodiments, the linker moiety is attached to an asparagine residue, at which position proteolytic cleavage occurs.

In particular embodiments, the peptide-drug conjugates have the structure of Formula 1 below:

R-Y-Z-Asn-Linker-D            (Formula I)

wherein
R comprises a substituent selected from the group consisting of
  i) an acyl group, a carbamoyl group, a sulfonyl group, phosphoryl group or an alkyl group derived from a $C_1$ to about $C_{20}$ linear, branched or alicyclic carboxylic acid, optionally substituted with from one to about five hydroxyl, amine, carboxyl, sulfonic, or phosphoryl groups,
  ii) a peptide with one to about fifty L- or D-amino acid residues, and
  iii) a polyethylene glycol with a molecular weight from 400 to about 40,000;
Y is an amino acid residue selected from the group consisting of Ala, Thr, Ser, Leu, Arg, Pro, Val, Tyr, Phe;
Z is an amino acid residue selected from the group consisting of Ala, Thr, Asn and Pro;
Asn is an asparagine residue;
Linker is a p-aminobenzyl carbamoyl moiety or a p-aminobenzyl carbonate moiety;
D is an anti-tumor drug moiety bonded to the Linker moiety, wherein the drug is selected from the group consisting of mitomycin, doxorubicin, aminopterin, actinomycin, bleomycin, 9-amino-camptothecin, $N^8$-acetyl spermidine, 1-(2-chloroethyl)-1,2-dimethanesulfonyl hydrazide, tallysomycin, cytarabine, etoposide, camptothecin, taxol, esperamicin, Podophyllotoxin, anguidine, vincristine, vinblastine, morpholine-doxorubicin, n-(5,5-diacetoxypentyl) doxorubicin, and derivatives thereof.

In particular embodiments of Formula I:
R comprises a substituent selected from the group consisting of
  i) an acyl group derived from a C1 to about C20 linear, branched or alicyclic carboxylic acid, optionally substituted with from one to about five hydroxyl, amine, carboxyl, sulfonic, or phosphoryl groups,
  ii) a peptide with one to about fifty L-amino acid residues, and
  iii) a polyethylene glycol with a molecular weight from 400 to about 40,000;
Y is an amino acid residue selected from the group consisting of Ala, Thr, Ser, Leu, Arg, Pro, Val, Tyr, Phe;

Z is an amino acid residue selected from the group consisting of Ala, Thr, Asn and Pro;
Asn is an asparagine residue;
Linker is a p-aminobenzylcarbamoyl moiety;
D is an anti-tumor drug moiety, wherein the drug is selected from the group consisting of mitomycin and doxorubicin.

In other particular embodiments of Formula I:
R comprises a substituent selected from the group consisting of
i) an acyl group, a carbamoyl group, a sulfonyl group, phosphoryl group or an alkyl group derived from a C1 to about C20 linear, branched or alicyclic carboxylic acid, optionally substituted with from one to about five hydroxyl, amine, carboxyl, sulfonic, or phosphoryl groups,
ii) a peptide with one to about fifty L- or D-amino acid residues, and
iii) a polyethylene glycol with a molecular weight from 400 to about 40,000;
Y is an amino acid residue selected from the group consisting of Ala, Thr, Ser, Leu, Arg, Pro, Val, Tyr, Phe;
Z is an amino acid residue selected from the group consisting of Ala, Thr, Asn and Pro;
Asn is an asparagine residue;
Linker is a p-aminobenzyl carbonate moiety; and
D is an anti-tumor drug moiety bonded to the Linker moiety and wherein the drug is camptothecin.

In still further embodiments, the invention comprises a dimeric peptide-drug conjugate of the formula shown in Formula II:

D'-Linker-Asn-Z-Y-R'-Y-Z-Asn-Linker-D        (Formula II)

Wherein D and D' are cytotoxic drug moieties which are the same are different from one another and are independently selected from the group consisting of mitomycin, doxorubicin, aminopterin, actinomycin, bleomycin, 9-amino-camptothecin, $N^8$-acetyl spermidine, 1-(2-chloroethyl)-1,2-dimethanesulfonyl hydrazide, tallysomycin, cytarabine, etoposide, camptothecin, taxol, esperamicin, Podophyllotoxin, anguidine, vincristine, vinblastine, morpholine-doxorubicin, n-(5,5-diacetoxy-pentyl) doxorubicin, and derivatives thereof;
Linker is a p-aminobenzyl carbamate moiety or p-aminobenzyl carbonate moiety, wherein the linkers may be the same or different;
R' comprises a substituent selected from the group consisting of
i) a bis-functional group selected from an acyl group, a carbamoyl group, a sulfonyl group, phosphoryl group or an alkyl group derived from a C1 to about $C_{20}$ linear, branched or alicyclic carboxylic acid, optionally substituted with from one to about five hydroxyl, amine, carboxyl, sulfonic, or phosphoryl groups,
ii) a peptide with one to about fifty L or D-amino acid residues, and
iii) a polyethylene glycol with a molecular weight from 400 to about 40,000; and
Y is an amino acid residue selected from the group consisting of Ala, Thr, Ser, Leu, Arg, Pro, Val, Tyr, Phe;
Asn is an asparagine residue; and
Z is an amino acid residue selected from the group consisting of Ala, Thr, Asn and Pro.

As will be appreciated, the conjugates of Formula II are essentially dimeric versions of the conjugates of Formula I, which can target two molecules of cytotoxic drug per conjugate to the targeted cells or tissue.

In further embodiments, the invention comprises a pharmaceutical composition which comprises at least one peptide-drug conjugate of Formula I or Formula II in at least one pharmaceutically-acceptable carrier.

In still further embodiments, the invention comprises a method of treating cancer in a mammal, which may be a human, which comprises administering an anti-tumor effective amount of the conjugate or pharmaceutical composition of the invention.

DETAILED DESCRIPTION OF THE INVENTION

"Mitomycin" as used here refers to members of the family of aziridine-containing drugs isolated from *Streptomyces caespitosus* or *Streptomyces lavendulae*, and includes specifically mitomycin C and mitomycin A.

"Doxorubicin" as used herein refers to members of the family of Anthracyclines derived from *Streptomyces* bacterium *Streptomyces peucetius* var. *caesius*, and includes doxorubicin, daunorubicin, epirubicin and idarubicin.

"Camptothecin" as used here refers to members of the family of alkaloids isolated from *Camptotheca acuminata* and its chemical derivatives, and includes camptothecin, irinotecan, topotecan and rubitecan.

The present invention provides tumor-specific, peptide-drug conjugates comprising a peptide moiety, a self-immolating linker which is p-aminobenzyl-carbamoyl or p-aminobenzyl carbonate (depending on the type of functional group contained in the drug to which the self-immolating linker is attached), and a cytotoxic drug moeity. The conjugates act as prodrugs in the sense that the conjugate is substantially inactive and non-toxic. The peptide moiety can be selectively cleaved by a protease enzyme in vivo to free the self-immolating linker/cytotoxic drug moiety. Upon such enzymatic cleavage, the self-immolating linker spontaneously hydrolyzes to yield the free drug in its active form, but more directed at the targeted milieu, such as the site of a tumor in a human patient. In this manner, the cytotoxic drug is targeted to a particular site in need of treatment, while cellular and tissue damage at sites other than the targeted site is reduced.

The cytotoxic drug moiety has a chemically reactive functional group by means of which the drug backbone is covalently bonded to the self-immolating linker. The functional group which links the cytotoxic drug to the self-immolating linker is such that, upon hydrolysis of the self-immolating linker, the cytotoxic drug is released in cytotoxically-active form. Such functional group may include, for example a primary amine, a secondary amine or hydroxyl. Cytotoxic drugs include mitomycin, doxorubicin, aminopterin, actinomycin, bleomycin, 9-amino-camptothecin, $N^8$-acetyl spermidine, 1-(2-chloroethyl)-1,2-dimethanesulfonyl hydrazide, tallysomycin, cytarabine, etoposide, camptothecin, taxol, esperamicin, Podophyllotoxin, anguidine, vincristine, vinblastine, morpholine-doxorubicin, n-(5,5-diacetoxy-pentyl) doxorubicin, and derivatives thereof. Preferred embodiments are based on mitomycin, doxorubincin and/or camptothecin.

In specific embodiments where the drug (D) is mitomycin, the peptide-drug conjugates have the structure as shown in Formula III (wherein R is defined as above and Ala is an alanine residue):

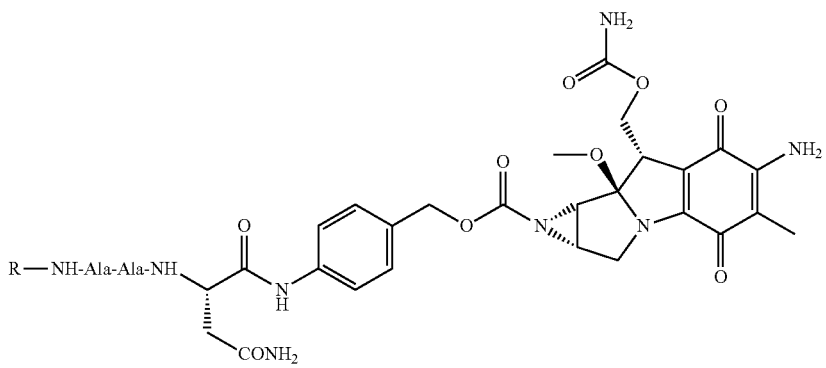

Formula III

In specific embodiments where the drug (D) is doxorubicin, the peptide-drug conjugates have the structure as shown in Formula IV (wherein R is defined as above and Ala is an alanine residue):

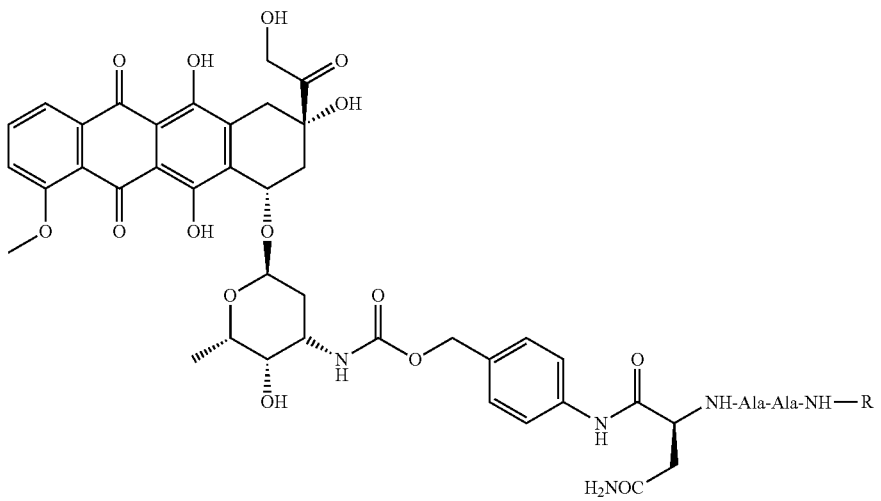

Formula IV

In specific embodiments where the drug (D) is camptothecin, the peptide-drug conjugates have the structure as shown in Formula V (wherein R, is defined as above and Ala is an alanine residue):

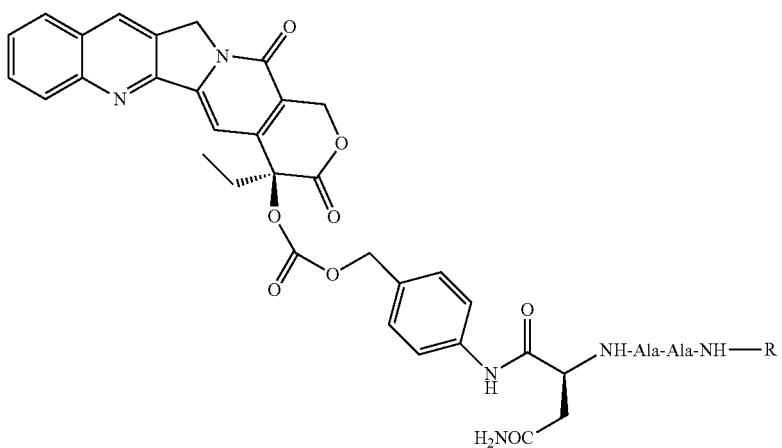

Formula V

In specific embodiments of dimeric conjugates where the drug (D) is mitomycin and drug (D') is doxorubicin, the peptide-drug conjugates have the structure as shown in Formula VI (wherein R' is defined as above and Ala is an alanine residue)

$N^\alpha$-[-(2-amide-2-oxoethoxy) acetic acid]-Ala-Ala-Asn-PABC-doxorubicin; and
$N^\alpha$-[-((2-amide-2-oxoethoxy)(methyl)amino) acetic acid]-Ala-Ala-Asn-PABC-doxorubicin; Wherein PABC is a p-aminobenzyl carbamoyl linker moiety.

Formula VI

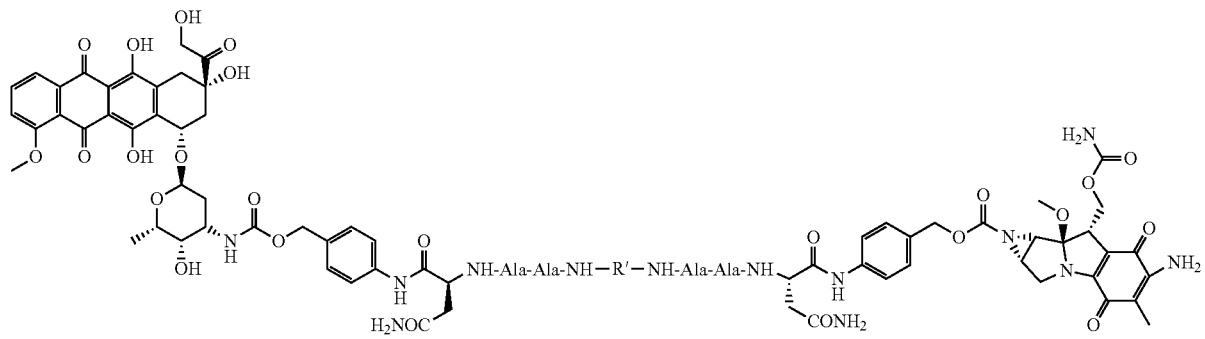

In specific embodiments of dimeric conjugates where the drug (D) is mitomycin and drug (D') is camptothecin, the peptide-drug conjugates have the structure as shown in Formula VII (wherein R' is defined as above and Ala is an alanine residue):

Other preferred conjugates of the invention include:
Ala-Ala-Asn-PABC-camptothecin;
$N^\alpha$-succinamic acid-Ala-Ala-Asn-PABC-camptothecin;
$N^\alpha$-[-(2-amide-2-oxoethoxy) acetic acid]-Ala-Ala-Asn-PABC-camptothecin; and Formula VII

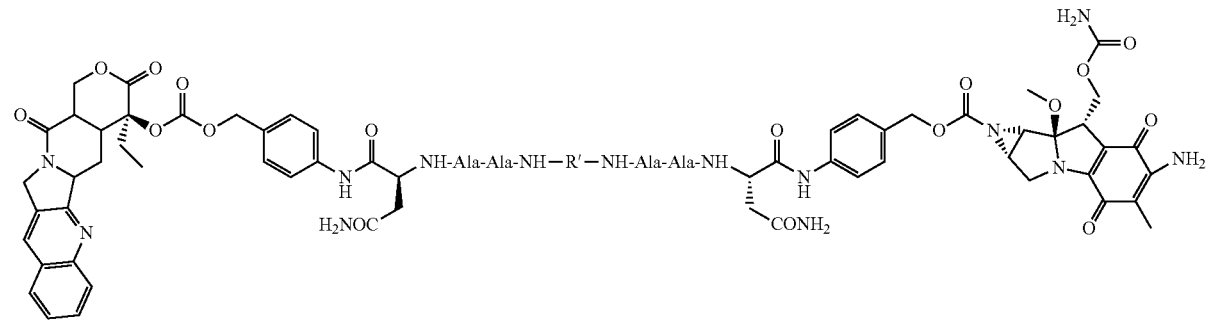

Preferred conjugates of the invention include:
Ala-Ala-Asn-PABC-mitomycin:
$N^\alpha$-succinamic acid-Ala-Ala-Asn-PABC-mitomycin:
$N^\alpha$-acetamide-Ala-Ala-Asn-PABC-mitomycin;
$N^\alpha$-butyramide-Ala-Ala-Asn-PABC-mitomycin;
$N^\alpha$-hexanamide-Ala-Ala-Asn-PABC-mitomycin;
$N^\alpha$-[-(2-amide-2-oxoethoxy) acetic acid]-Ala-Ala-Asn-PABC-mitomycin; and
$N^\alpha$-[-((2-amide-2-oxoethoxy)(methyl)amino) acetic acid]-Ala-Ala-Asn-PABC-mitomycin; Ala-Ala-Asn-PABC-doxorubicin;
$N^\alpha$-succinamic acid-Ala-Ala-Asn-PABC-doxorubicin;
$N^\alpha$-acetamide-Ala-Ala-Asn-PABC-doxorubicin;
$N^\alpha$-butyramide-Ala-Ala-Asn-PABC-doxorubicin; and
$N^\alpha$-hexanamide-Ala-Ala-Asn-PABC-doxorubicin;

$N^\alpha$-[-((2-amide-2-oxoethoxy)(methyl)amino) acetic acid]-Ala-Ala-Asn-PABC-camptothecin
Wherein PABC is a p-aminobenzyl carbonate moiety.
Preferred dimeric conjugates include:
$N^1$-Ala-Ala-Asn-PABC-mitomycin, $N^4$-Ala-Ala-Asn-PABC-doxorubicin-succinamide:
$N^1$-Ala-Ala-Asn-PABC-mitomycin, $N^5$-Ala-Ala-Asn-PABC-doxorubicin-bis($O^\alpha$)-acetamide:
$N^1$-Ala-Ala-Asn-PABC-mitomycin, $N^5$-Ala-Ala-Asn-PABC-doxorubicin-bis($N^\alpha$-methyl)-acetamide;
$N^1$-Ala-Ala-Asn-PABC-mitomycin, $N^4$-Ala-Ala-Asn-PABC-camptothecin-succinamide;
$N^1$-Ala-Ala-Asn-PABC-mitomycin, $N^5$-Ala-Ala-Asn-PABC-camptothecin-bis($O^\alpha$)-acetamide; and
$N^1$-Ala-Ala-Asn-PABC-mitomycin, $N^5$-Ala-Ala-Asn-PABC-camptothecin-bis($N^\alpha$-methyl)-acetamide.

Wherein PABC is a p-aminobenzyl carbamoyl or p-aminobenzyl carbonate linker moiety.

Preparation of Peptide-Drug Conjugates

In general, the peptide-drug conjugates of Formula I and Formula II may be prepared using available materials and conventional organic synthesis techniques. For example, cytotoxic drugs of the type described are commercially-available and their synthesis is described in the scientific literature.

Generally, the peptide-drug conjugates of the present invention may be constructed by covalently attaching the drug moiety to the peptide sequence through the self-immolating linker. The specific synthetic routes of preparation shown below are exemplary of those which may be utilized.

Synthesis scheme 1 shows a synthetic route for producing peptide-mitomycin conjugates:

Synthesis Scheme 1

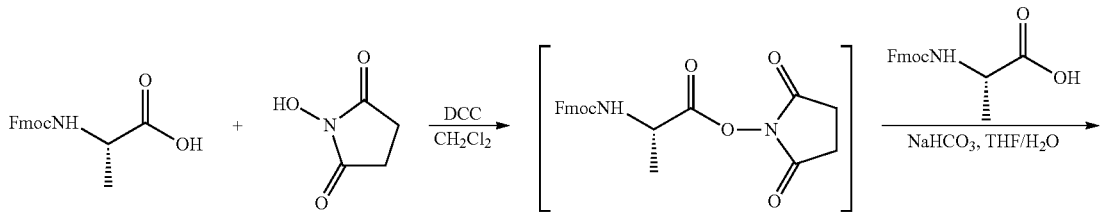

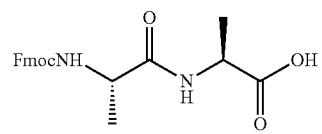

[1]

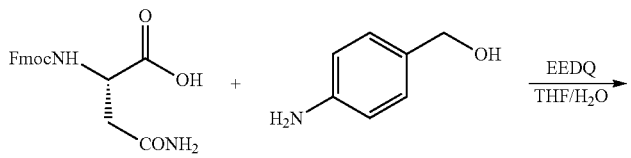

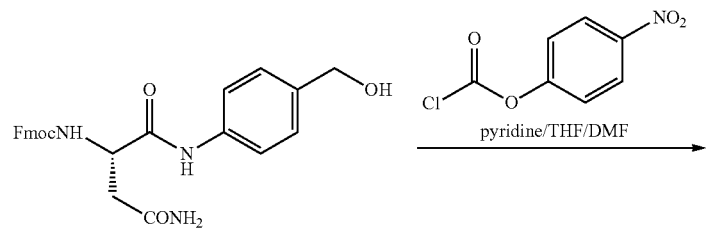

[2]

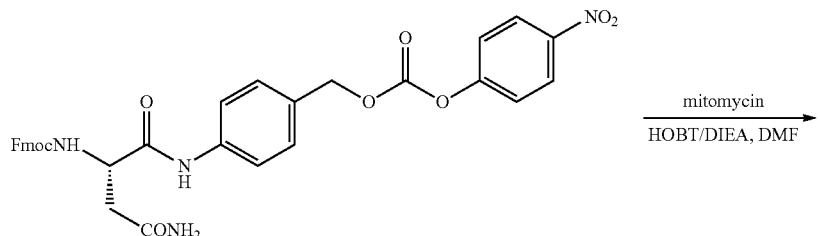

[3]

-continued
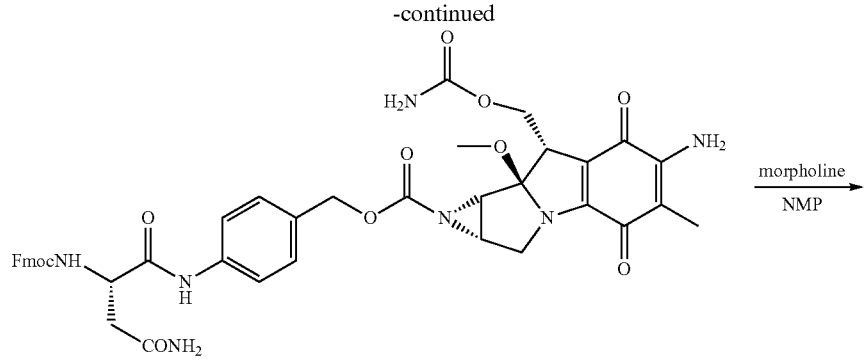
[4]
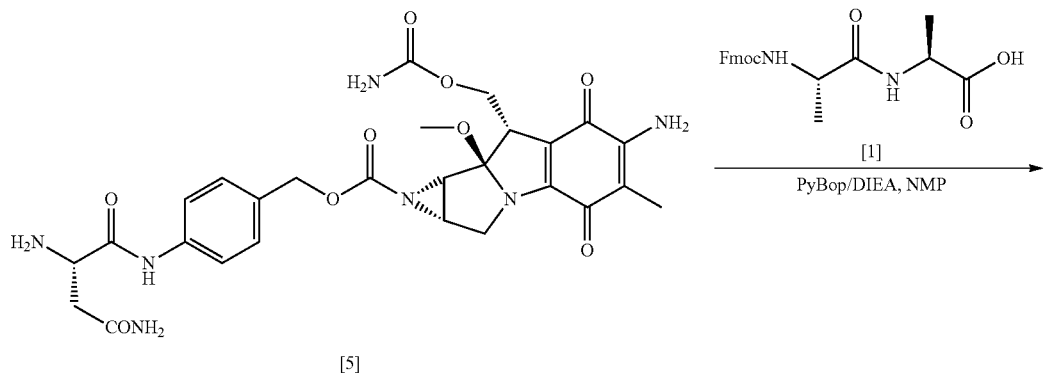
[5]
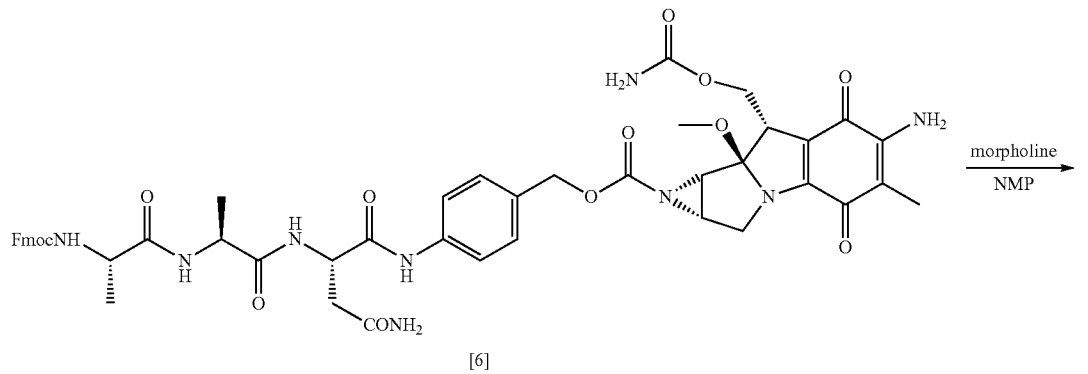
[6]
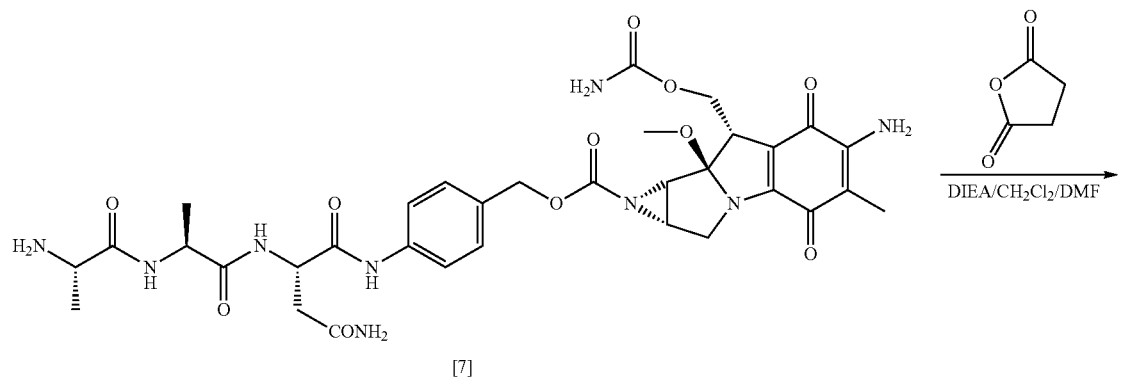
[7]

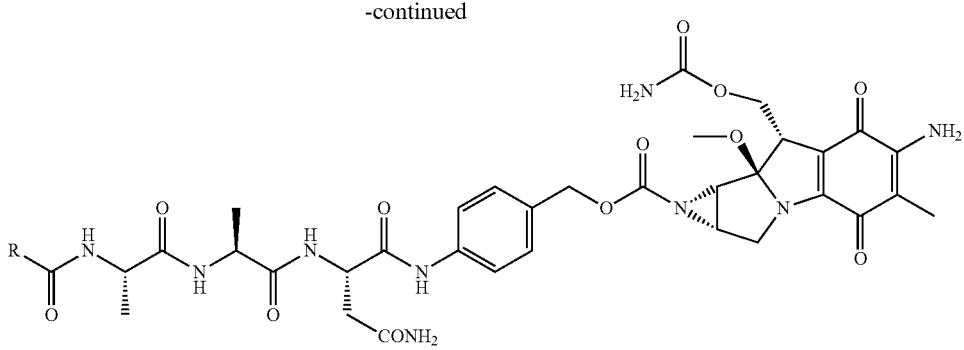
[8] R = CH₂CH₂COOH
[9] R = CH₃
[10] R = CH₂CH₂CH₃
[11] R = CH₂CH₂CH₂CH₂CH₃
[12] R = CH₂OCH₂COOH
[13] R = CH₂N(CH₃)CH₂COOH
Synthesis scheme 2 shows a synthetic route for producing peptide-doxorubicin conjugates:
Synthesis Scheme 2
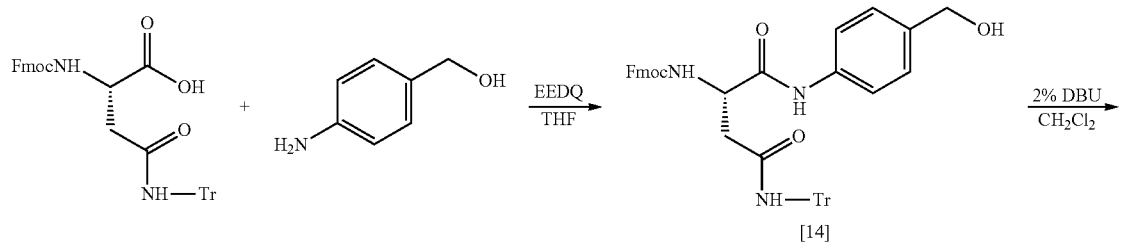
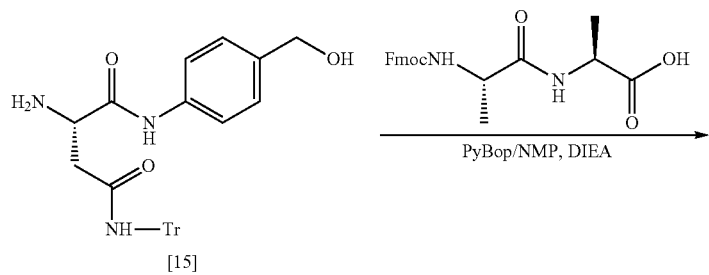
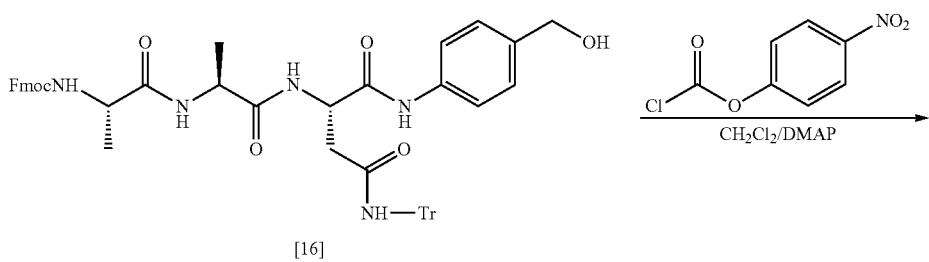

-continued
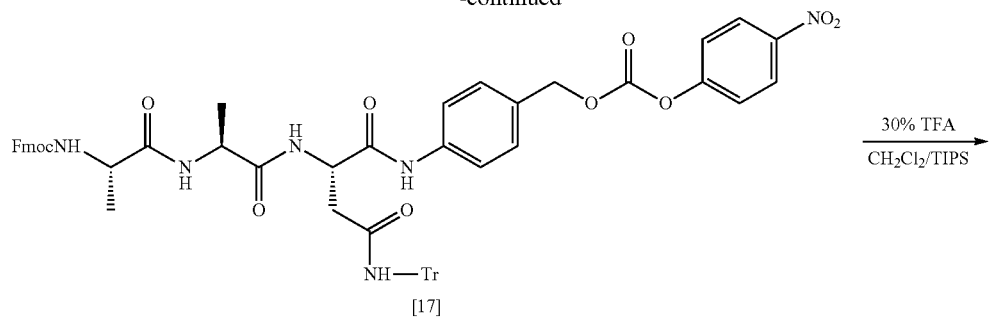
[17]
$$\xrightarrow{\text{30\% TFA}}_{\text{CH}_2\text{Cl}_2/\text{TIPS}}$$
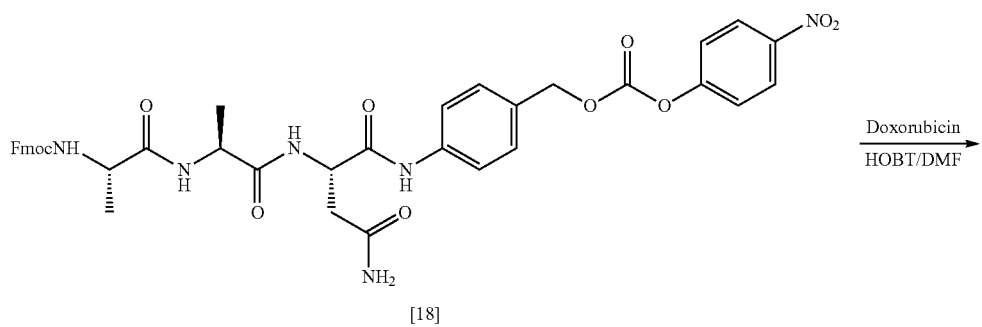
[18]
$$\xrightarrow{\text{Doxorubicin}}_{\text{HOBT/DMF}}$$
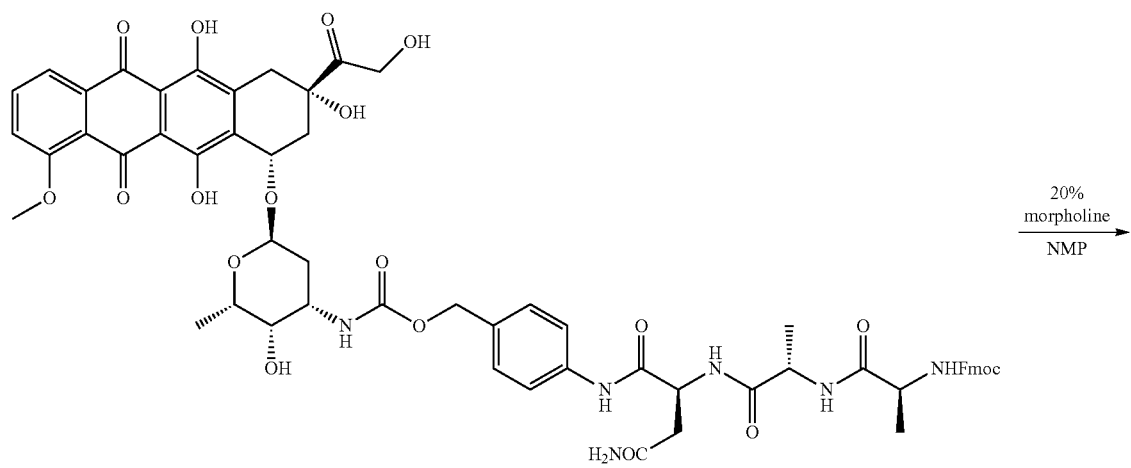
[19]
$$\xrightarrow{\text{20\% morpholine}}_{\text{NMP}}$$
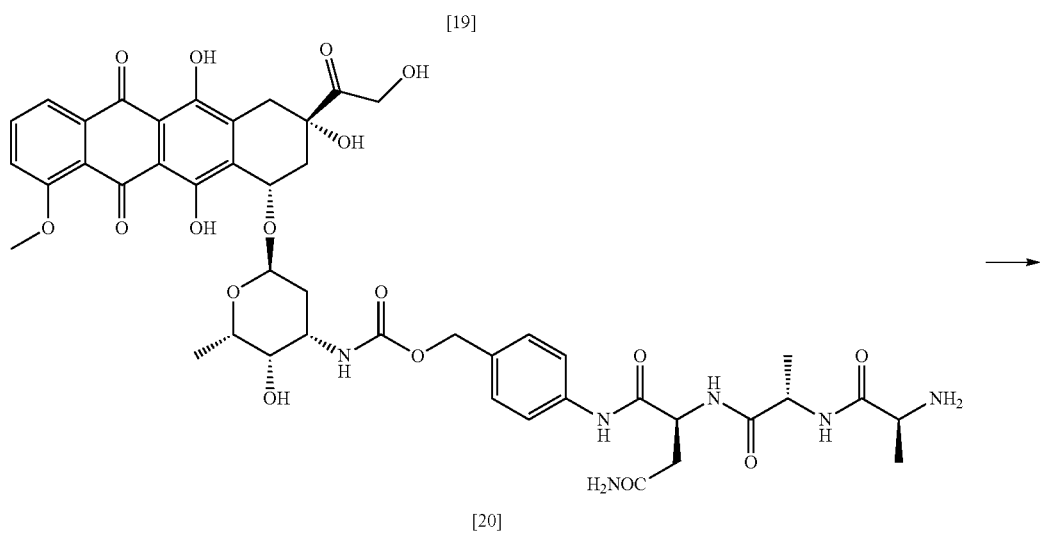
[20]
$\longrightarrow$

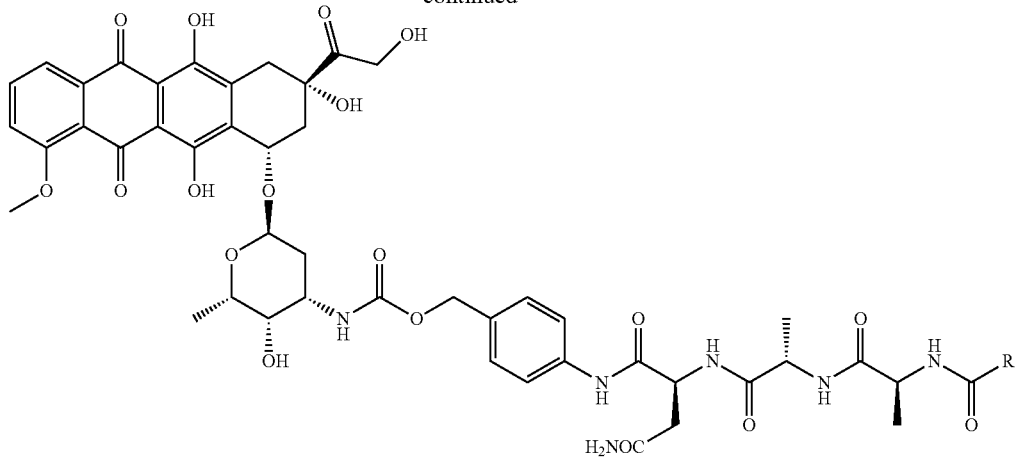
[21] R = CH$_2$CH$_2$COOH
[22] R = CH$_2$OCH$_2$COOH
[23] R = CH$_2$N(CH$_3$)CH$_2$COOH
Synthesis Scheme 3 shows a synthetic route for producing peptide-camptothecin conjugates:
Synthesis Scheme 3
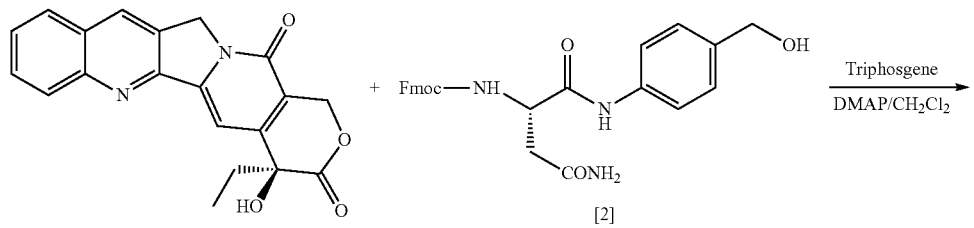
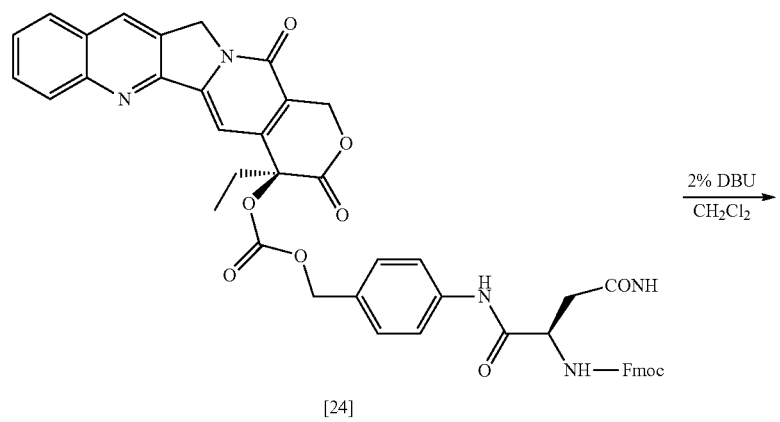

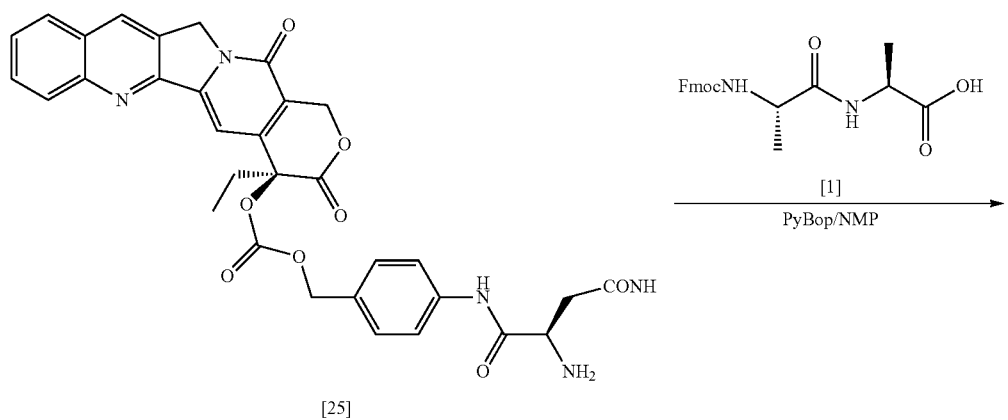
[25]
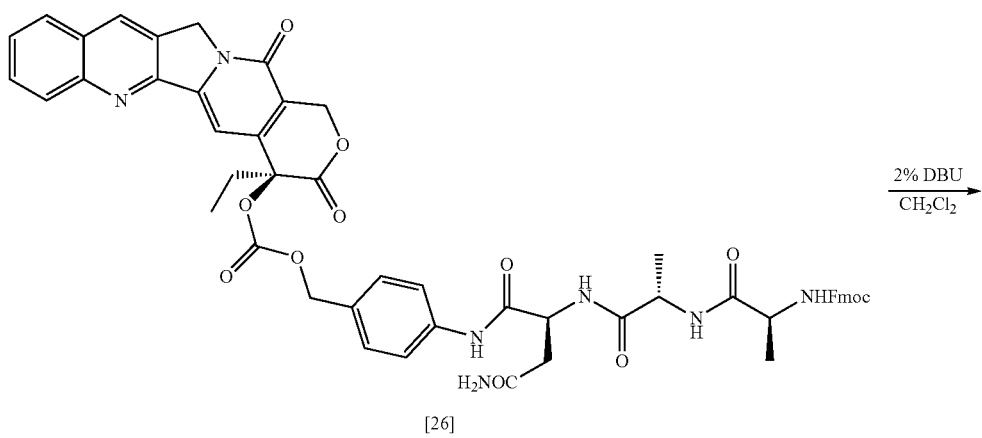
[26]
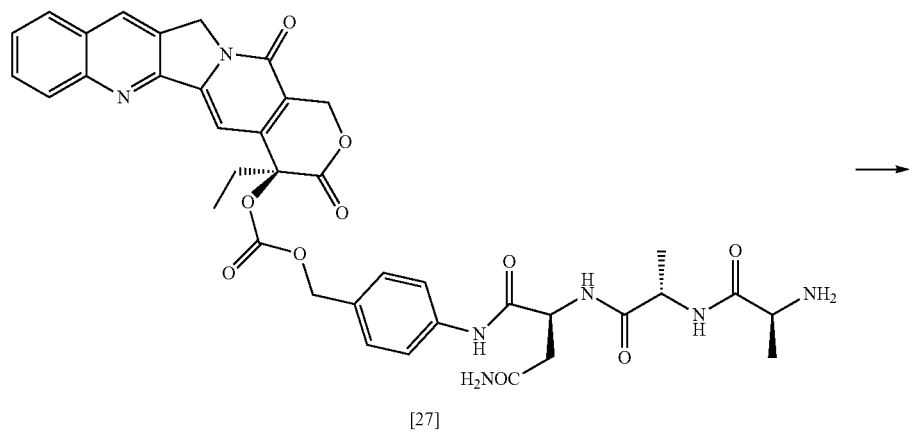
[27]

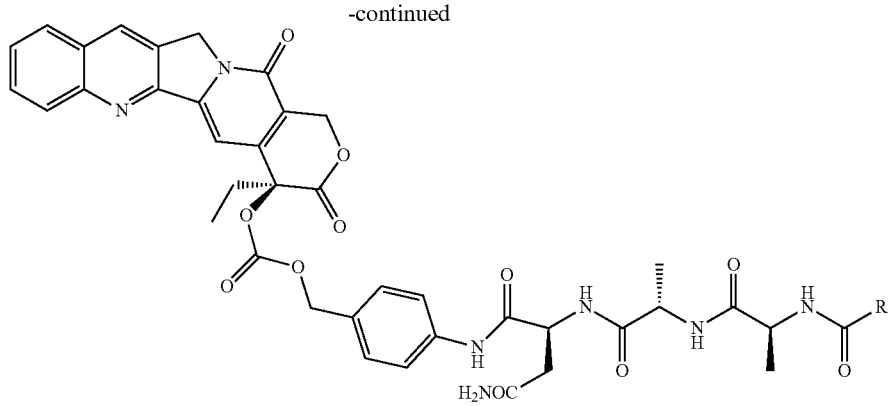
[28] R = CH₂CH₂COOH
[29] R = CH₂OCH₂COOH
[29] R = CH₂N(CH₃)CH₂COOH
Synthesis Scheme 4 shows a synthetic route for producing doxorubicin-peptide-mitomycin conjugates (dimeric conjugate):
Synthesis Scheme 4
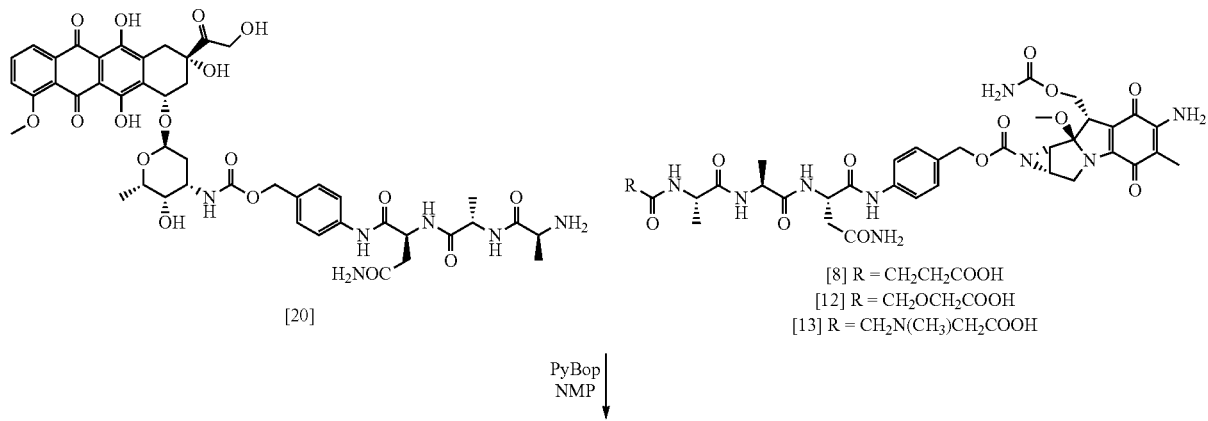
[20]
[8] R = CH₂CH₂COOH
[12] R = CH₂OCH₂COOH
[13] R = CH₂N(CH₃)CH₂COOH
PyBop
NMP
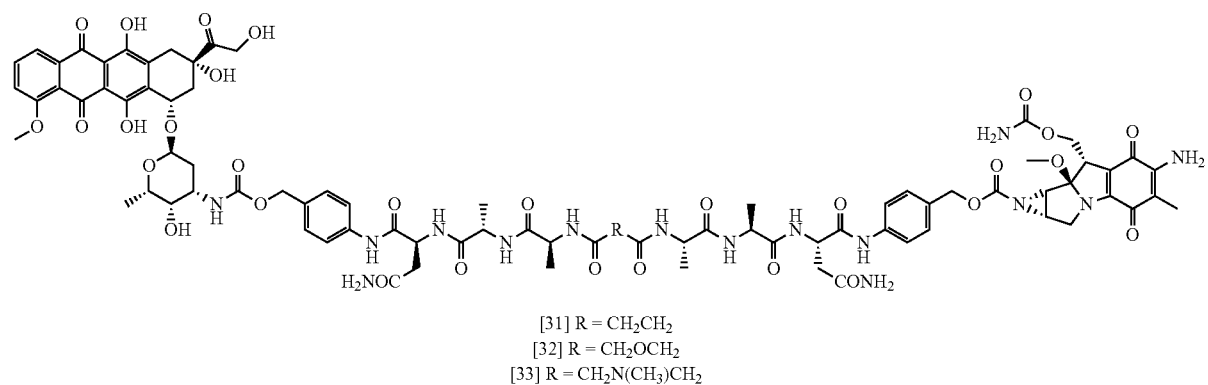
[31] R = CH₂CH₂
[32] R = CH₂OCH₂
[33] R = CH₂N(CH₃)CH₂

Synthesis Scheme 5 shows a synthetic route for producing camptothecin-peptide-mitomycin conjugates (dimeric conjugates):

f) The final peptide-drug conjugates were obtained by acylation with various anhydrides, acyl chlorides or carboxylic acids by peptide coupling methods.

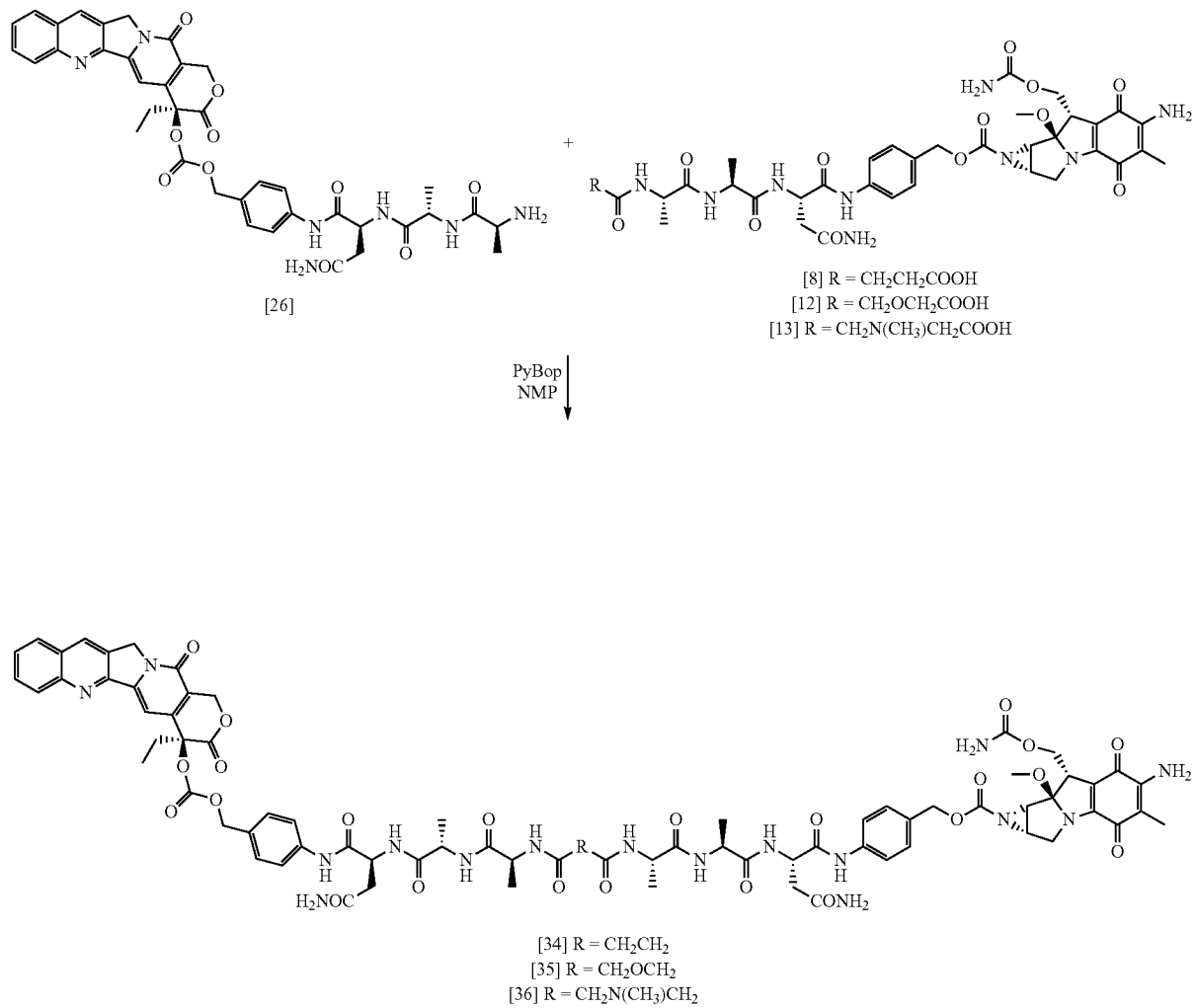

In general for the described synthesis reactions:
a) Standard peptide synthesis methods were employed for Fmoc and trityl deportation, and peptide coupling;
b) The self-immolating linker was attached to amino acid by reacting $N^\alpha$-Fmoc-Asn or trityl protected $N^\alpha$-Fmoc-Asn with p-aminobenzyl alcohol, using EEDQ as coupling reagent in organic/aqueous solvent mixture;
c) The activated carbonate of p-aminobenzyl alcohol could be obtained by reacting p-nitrophenyl chloroformate with $N^\alpha$-Fmoc-Asn-PAB-OH or $N^\alpha$-Fmoc-Ala-Ala-N-Trityl-Asn-PAB-OH;
d) Peptide drug conjugates of mitomycin and doxorubicin were obtained by reacting with corresponding activated carbonate of $N^\alpha$-Fmoc-Asn-PABC-PNP or $N^\alpha$-Fmoc-Ala-Ala-Asn-PABC-PNP in DMF in the presence of HOBT;
e) For the synthesis of camptothecin conjugates, camptothecin was reacted with triphosgene to provide canptothecin chloroformate in situ, which was then coupled with $N^\alpha$-Fmoc-Asn-PAB-OH to obtain corresponding $N^\alpha$-Fmoc-Asn-PABC-camptothecin;

Synthesized final conjugates can be purified by various methods including silica column chromatography, HPLC, ion exchange chromatography, acid/base precipitation and crystallization.

The final conjugates may be characterized by $^1$H-NMR, $^{13}$C-NMR, MS, LC/MS, UV/VIS, and/or IR.

Many of the disclosed conjugates can exist as hydrochloride or other salts. Those skilled in medicinal chemistry will appreciate that the choice of salt is not critical, and other pharmaceutically-acceptable salts can be prepared by well-known methods and can be utilized in the preparation of pharmaceutical compositions. See, e.g., Handbook of Pharmaceutical Salts: Properties, Selection and Use. (P. Heinrich Stahl and Camille G. Wermuth, eds.) International Union of Pure and Applied Chemistry, Wiley-VCH 2002 and L. D. Bighley, S. M. Berge, D. C. Monkhouse, in "Encyclopedia of Pharmaceutical Technology". Eds. J. Swarbrick and J. C. Boylan, Vol. 13, Marcel Dekker, Inc., New York, Basel, Hong Kong 1995, pp. 453-499.

In addition, those skilled in the art will appreciate that not only a variety of salts can be produced and used, but also, hydrates, solvates, and polymorphs can be produced from the conjugates disclosed herein. Also, various isotopically-substituted variants (through, e.g., substitution of deuterium for hydrogen, $^{13}C$ for carbon, $^{15}N$ for nitrogen) can also be readily produced. Such derivatives are contemplated within the scope of this disclosure.

To prepare the pharmaceutical compositions of the invention, one or more of the conjugates is combined with at least one pharmaceutically acceptable carrier. "Pharmaceutically acceptable carriers" refer to biocompatible compounds that are suitable for a particular route of administration for a pharmacologically effective substance. They include stabilizing agents, wetting and emulsifying agents, salts for varying osmolarity, encapsulating agents, buffers, and skin penetration enhancers. Examples of pharmaceutically acceptable carriers are described in Remington's Pharmaceutical Sciences (Alfonso R. Gennaro, ed., 18 th edition, 1990). The particular choice of carrier(s) depends upon the specific therapy which is contemplated. Various formulations for pharmaceutical compositions and components thereof are described in US published patent application 2014/0057844, the disclosure of which is incorporated by reference.

The selection of cytotoxic drug moiety in the conjugates is guided by the type of cancer to be treated. For treatment of a specific type of cancer or tumor, the cytotoxic drug moiety should be based on a cytotoxic drug effective to treat such type of cancer. For example, the drug conjugates based on mitomycin may be used to treat cancers in accordance with, or guided by, mitomycin administration protocols which are currently known and recommended in the art.

The conjugates, compositions, and methods of the invention may be used to treat different types of cancers, including but not limited to bladder cancer, breast cancers, cervical cancer, ovarian cancer, stomach cancer, pancreatic cancer, lung cancer, liver cancer, oesophageal cancer, bowel cancer; skin cancer, and prostate cancer.

Routes of administration include injection, oral administration, buccal administration, parenteral administration, inhalation, and rectal administration.

Dosage of the conjugates to be administered, and particular routes and regimens of administration, depend upon the type of cancer to be treated and the circumstances of particular cancer conditions, but can be determined by persons skilled in the art.

The conjugates of the invention may be used in combination with each other and in combination with other chemotherapeutic agents or treatments. For example, a therapy using the conjugates of the invention may be used in combination with radiation therapy.

The examples which follow illustrate certain embodiments of the invention and should be considered as illustrative but not limiting on the scope of the invention.

EXAMPLES

Biological Activity

Representative peptide-drug conjugates of the present invention were tested in both in vitro and in vivo system to determine their biological activity. In these tests, the potency of the conjugates of the cytotoxic drugs was determined by measuring the cytotoxicity of the conjugates against cells of human cancer origin. One skilled in the art will recognize that any tumor cell line expressing the desired tumor associated proteases (proteases which cleave the conjugates of the invention to release drug in active form) could be used instead of the specific tumor cell lines used in the following analysis. The following describes representative tests used and the results obtained.

Test I

Human Plasma Stability

20 µL of 500 µM peptide-drug conjugate $N^\alpha$-succinamic acid-Ala-Ala-Asn-PABC-mitomycin [herein compound 8] in DMSO stock solution was diluted to 1 mL with human plasma (final concentration: 10 µM, 2% DMSO), and the mixture was incubated at 37° C. 100 µL aliquots were removed at the time points of 0, 0.25, 0.5, 1, 2, 4, 6 hours and diluted with 400 µL cold acetonitrile containing tolbutamide (200 ng/mL) as internal standard. The samples were centrifuged at 14,000 rpm for 4 minutes. 100 µL of above supernatants were diluted with 300 µL of 0.1% formic acid HPLC water and 10 µL was taken for LC/MS/MS analysis (column: C-18; mobile phase: 0.1% formic acid in water/ 0.1% formic acid in acetonitrile; ion transition: Q1 ion (m/z)=840.5, Q2 ion (m/z)=462.2). As shown in FIG. 1, the peptide-drug conjugate is relatively stable in human plasma with a half life greater than 15 hours (T1/2>15 h). Less than 2% of free drug mitomycin was detected.

Test II

In Vitro Cytotoxicity Assay

Monolayer cultures of human carcinoma cells were harvested using trypsin-EDTA, and the cells counted and resuspended to $1\times10^5$/mL in RPMI-1640 or DMEM containing 10% FBS. Cells (0.1 mL/well) were added to each well of 96 well microtiter plates and incubated overnight at 37° C. in a humidified atmosphere of 5% $CO_2$. Media was removed from the plates and serial dilutions of mitomycin or conjugates in medium (final DMSO concentration <0.1%) was added to the wells. All dilutions were performed in triplicate. The drug treated cells were incubated for another 72 hours at 37° C. in a humidified atmosphere of 5% $CO_2$. 50 µL of cold TCA (50%, wt/vol) was added to each well and incubated the plates at 4° C. for 1 hour. The plates were washed with slow-running tap water for three times and the dried at room temperature. 50 µL of Sulforhodamine B solution (0.4%, wt/vol) was added to each well and the plates were left at room temperature for 1 hour. The plates were rinsed with acetic acid solution (1%, vol/vol) to remove the unbound dye and dried at room temperature. 200 µL of 10 mM Tris base solution was added to each well and the plates were shaken on a gyratory shaker for 15 minutes to solubilize the protein-bound dye. Well optical density at 510 nm was measured in a microplate reader, and the $IC_{50}$ was calculated by GraphPad from three separated experiments with triplicate in each experiment and expressed as mean (Table 1).

TABLE 1

| | $IC_{50}$ (µM, n = 3) | |
|---|---|---|
| Sample | HCT116 | HepG2 |
| mitomycin | 0.116 | 0.143 |
| $N^\alpha$-succinamicacid-Ala-Ala-Asn-PABC-mitomycin [compound 8] | 6.65 | 2.48 |
| $N^\alpha$-acetamide-Ala-Ala-Asn-PABC-mitomycin [compound 9] | 5.37 | 4.17 |
| $N^\alpha$-butyramide-Ala-Ala-Asn-PABC-mitomycin [compound 10] | 8.85 | 8.16 |
| $N^\alpha$-hexanamide-Ala-Ala-Asn-PABC-mitomycin [compound 11] | 5.95 | 4.91 |

The HCT116 and HepG2 human carcinoma cell lines assays reveal that the cytotoxicity of peptide-drug conjugates was reduced by 76- to 17-fold as compared with parent drug mitomycin, depending on different tumor cell lines. Tumor associated protease legumain is over-expressed in the tumor microenvironment of solid tumor in hypoxic and acidic conditions. However, some level of legumain expression of both HCT116 and HepG2 cell lines in cell culture was previously reported, which may result in the residual activity of peptide-drug conjugate as observed in this assay.

Test III

In Vivo Maximum Tolerated Dose (MTD) in Balb/c Mice

Figure 2:
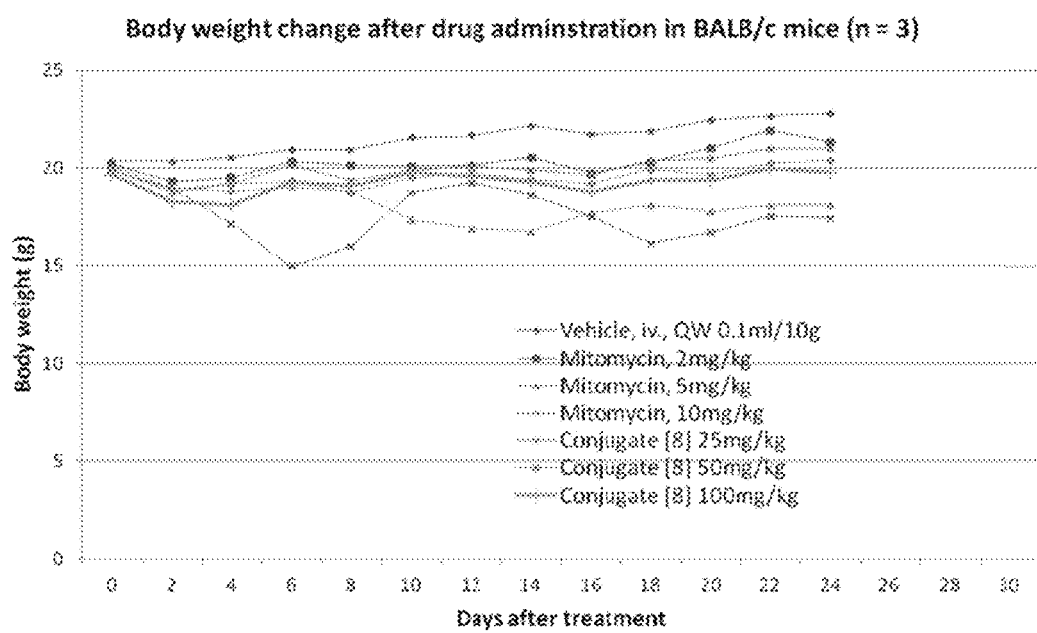
FIG. 2 is a graph showing the body weight of Balb/c mice as a function of time after administration of $N^\alpha$-succinamic acid-Ala-Ala-Asn-PABC-mitomycin.

The tolerability of mitomycin and its peptide-drug conjugate $N^\alpha$-succinamic acid-Ala-Ala-Asn-PABC-mitomycin [compound 8] as single agent were evaluated separately in Balb/c mice. The results of body weights in different groups at different time points after treatment are shown in FIG. 2.

In 10 mg/kg, once per week dose group of mitomycin, animal death was observed. In the 5 mg/kg group, the mice displayed behaviors of piloerection and retardation. The body weight loss (>15%) was observed in 5 mg/kg mitomycin group. Meanwhile, no abnormal appearance and body weight (<10%) was observed for peptide-drug conjugate $N^\alpha$-succinamic acid-Ala-Ala-Asn-PABC-mitomycin [8] at the dose groups of 25, 50 and 100 mg/kg, once per week, three injections total for 24 days. The murine toxicity study revealed that peptide-drug conjugate N-succinamic acid-Ala-Ala-Asn-PABC-mitomycin [8] is much less toxic than parent drug mitomycin in vivo. The mice maximum tolerated dose (MTD) of peptide-drug conjugate increases by at least 20-fold as compared with the parent drug mitomycin.

Test IV

In Vivo Antitumor Activity

Figure 3:
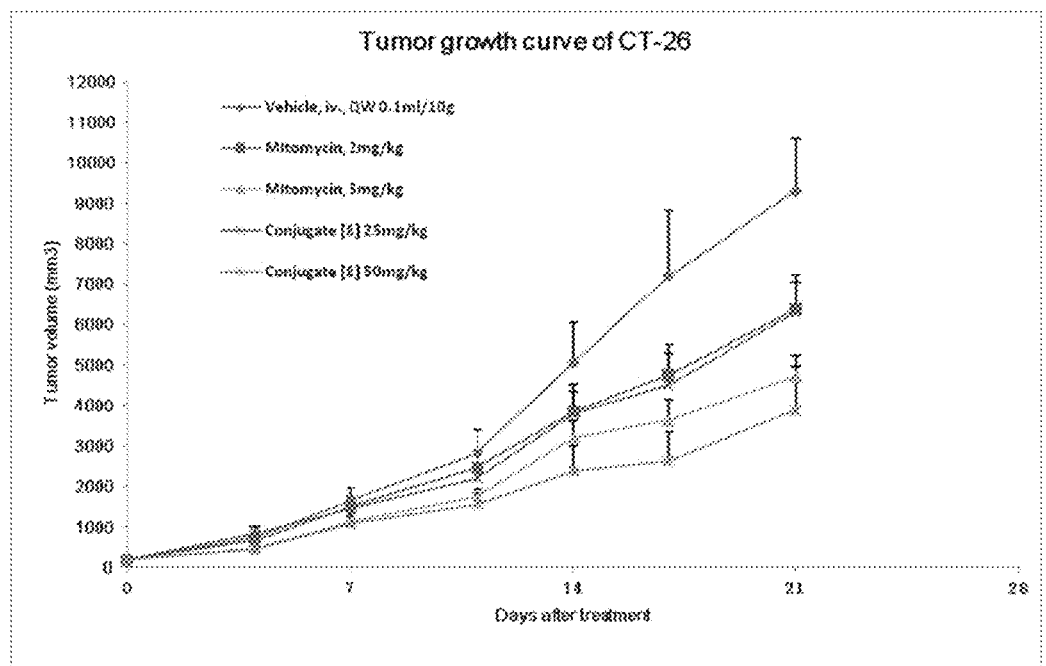
FIG. 3 is a graph showing the tumor growth curve of the subcutaneous CT-26 syngenic colon cancer model in Balb/c mice after administration of $N^\alpha$-succinamic acid-Ala-Ala-Asn-PABC-mitomycin.

The tumoricidal effect of peptide-drug conjugate $N^\alpha$-succinamic acid-Ala-Ala-Asn-PABC-mitomycin [8] was evaluated on subcutaneous CT-26 syngenic colon cancer model in Balb/c mice. Each mouse was inoculated subcutaneously at the right flank region with CT-26 tumor cells ($5 \times 10^5$) in 0.1 mL of PBS. When the mean tumor size reached approximately 180 mm$^3$ (after around 10 days), the CT-26 tumor mice were treated through intravenous administration with: vehicle (2% DMA and 98% of 40% 2HP-P3-CD), mitomycin (2 mg/kg; 5 mg/kg, QW) and conjugate $N^\alpha$-succinamic acid-Ala-Ala-Asn-PABC-mitomycin [8](25 mg/kg; 50 mg/kg, QW) for three weeks, total of three injections per mouse. The tumor growth curve of CT-26 model is shown in FIG. 3.

As reported previously, even though CT-26 cells has week expression of tumor associated protease legumain in vitro, it is abundantly expressed in vivo in TMEs on the surface of viable endothelial cells and tumor-associated macrophages in CT-26 solid tumor microenvironment, as the legumain expression is induced under hypoxia and stress condition. Legumain specific activation conjugate $N^\alpha$-succinamic acid-Ala-Ala-Asn-PABC-mitomycin [8] demonstrated strong antitumor efficacy on subcutaneous CT-26 syngenic colon cancer model in Balb/c mice as shown in FIG. 3. At 50 mg/kg, dose, which is much lower than its MTD, the conjugate significantly inhibits the tumor growth versus untreated control (T/C=36.4%, p<0.01). While at its MTD dose (5 mg/kg), the parent drug mitomycin demonstrated much weaker tumor growth inhibition effect (T/C=50.4%). Therefore, in vivo experiments show that the peptide-mitomycin conjugate of the present invention produce antitumor activity with greater potency and less toxicity to the host than parent drug mitomycin.

Synthesis Examples

Example 1

Preparation of $N^\alpha$-Fmoc-Ala-Ala [1]

A solution of $N^\alpha$-Fmoc-Ala (1.58 g, 5.0 mmoles), N-hydroxyl succinimide (0.63 g, 5.5 mmoles) and DCC (1.03 g, 5.0 mmoles) in CH$_2$Cl$_2$ (50 mL) were stirred at 5° C. for 6 hours. The DCU was filtered out and the filtrate was concentrated. Residue was re-dissolved in THF (50 mL) and kept in refrigerator (4° C.) overnight. More DCU was filtered off and the THF solution was added to a solution of alanine (0.99 g, 7.5 mmoles) and NaHCO$_3$ (1.68 g, 20 mmoles) in 25% THF/H$_2$O (80 mL). The reaction mixture was stirred vigorously at 25° C. for 5 hours. THF was removed by concentration and the aqueous suspension was adjusted to pH4 with concentrated HCl. The aqueous suspension was stirred at 25° C. for another 3 hours and the precipitate was collected by filtration, rinsed thoroughly with de-salt water and was dried in vacuum over KOH to give a white solid product (1.77 g, 83.7% yield).

LC/MS: (MH)$^+$=383

Example 2

Preparation of $N^\alpha$-Fmoc-Asn-PAB-OH [2]

A solution of $N^\alpha$-Fmoc-Asn (1.77 g, 5.0 mmoles), p-aminobenzyl alcohol (0.86 g, 7.0 mmoles) and EEDQ (1.48 g, 6 mmoles) in THF/H2O (100/20 mL) were stirred at room temperature overnight. Additional amount of EEDQ (0.61 g, 2.5 mmoles) was added and stirred for another 24 hours. THF was removed by concentration and the residue suspension was diluted with NaOH/NaHCO$_3$ aqueous solution (⅔ g, 200 mL) and stirred for 3 hours. The precipitate was collected by filtration, rinsed with water and re-suspended in 10% citric acid (150 mL). Precipitate was collected by filtration, rinsed with 10% citric acid followed by de-salt water and dried in vacuum. The above obtained solid was triturated in ethyl acetate (100 mL). Solid was collected by filtration and dried in vacuum to give an off-white product (0.95 g, 40% yield).

LC/MS: (MH)$^+$=460

Example 3

Preparation of $N^\alpha$-Fmoc-Asn-PABC-PNP [3]

N-Fmoc-Asn-PAB-OH [2](0.75 g, 1.6 mmoles) in dry THF/DMF (50/5 mL) at room temperature was treated with p-nitrophenyl chloroformate (0.4 g, 2.0 mmloes) and pyridine (0.15 g, 2.0 mmoles). After 16 hours, additional amount of p-nitrophenyl chloroformate (0.2 g, 1.0 mmoles) was added and the reaction solution was stirred for another 6 hours. The above solution was diluted with ethyl acetate (250 mL) and was washed with 5% citric acid (2×100 mL) followed by brine, dried with Na$_2$SO$_4$, and evaporated to dryness. The residue was triturated in 50% EA/Hexane and the solid was collected by filtration to give an off-yellow product (0.8 g, 81% yield).

LC/MS: (MH)$^+$=625

Example 4

Preparation of $N^\alpha$-Fmoc-Asn-PABC-mitomycin [4]

$N^\alpha$-Fmoc-Asn-PABC-PNP [3](624 mg, 1.0 mmoles) and mitomycin (400 mg, 1.2 mmoles) in dry DMF (15 mL) at room temperature were treated with HOBT (675 mg, 5.0 mmoles) and DIEA (650 mg, 5.0 mmoles) for 4 hours. Reaction mixture was diluted with ethyl acetate (150 mL) and washed three times with NaOH/NaHCO$_3$ (¼ g, 200 mL) followed by brine. The organic layer was dried with Na$_2$SO$_4$ and concentrated to dryness under reduced pressure. The residue was triturated in 50% ethyl acetate/hexane (50 mL) and the solid was collected by filtration, rinsed with ethyl acetate/hexane and dried in vacuum to give a purple product (635 mg, 76.3% yield).
LC/MS: (MH)$^+$=820

Example 5

Preparation of Asn-PABC-mitomycin [5]

N$^\alpha$-Fmoc-Asn-PABC-mitomycin [4](624 mg, 0.76 mmoles) was treated with 20% morpholine/NMP (15 mL) at room temperature. After 30 minutes, 50% ethyl acetate/hexane (100 mL) was added and the supernatant was removed. The above process was repeated twice. The residue was re-dissolved in methanol (25 mL) and the solvent was evaporated under reduced pressure to dryness. Residue was triturated in 50% ethyl acetate/hexane (100 mL) and stirred at room temperature overnight. Solid was collected by filtration, rinsed the ethyl acetate/hexane and dried in vacuum to give a purple product (440 mg, 95.6% yield).
LC/MS: (MH)$^+$=598

Example 6

Preparation of N-Fmoc-Ala-Ala-Asn-PABC-mitomycin [6]

Asn-PABC-mitomycin [5](440 mg, 0.73 mmoles) and N-Fmoc-Ala-Ala [1](286 mg, 0.75 mmoles) in NMP (15 mL) were treated with PyBop (390 mg, 0.75 mmoles) and DIEA (585 mg, 4.5 mmoles) at room temperature. After 1 hour, the reaction mixture was diluted with ethyl acetate (200 mL). The organic solution was washed with 5% citric acid (3×100 mL), brine and dried with Na$_2$SO$_4$. Solvent was evaporated under reduced pressure and the residue was triturated in 50% ethyl acetate/hexane (100 mL) and stirred at room temperature overnight. Solid was collected by filtration and re-suspended in ethyl acetate (50 mL) and sonicated. Solid was collected by filtration, rinsed thoroughly with ethyl acetate and dried in vacuum to give a purple product (530 mg, 75.4% yiled).
LC/MS: (MH)$^+$=962

Example 7

Preparation of Ala-Ala-Asn-PABC-mitomycin [7]

N$^\alpha$-Fmoc-Ala-Ala-Asn-PABC-mitomycin [6](481 mg, 0.5 mmloes) was treated in 20% morpholine/NMP (10 mL) at room temperature. After 30 minutes, 50% ethyl acetate/hexane (150 mL) was added and stirred for 1 hour. The supernatant was removed and the residue was triturated in CH$_2$Cl$_2$ (50 mL). Solid was collected by filtration and re-dissolved in methanol (20 mL). Solvent was evaporated under reduced pressure and the residue was triturated in ethyl acetate. Solid was collected by filtration, rinsed thoroughly with ethyl acetate and dried in vacuum to give a purple product (277 mg, 75% yield).
LC/MS: (MH)$^+$=740

Example 8

Preparation of N$^\alpha$-succinamic acid-Ala-Ala-Asn-PABC-mitomycin [8]

Ala-Ala-Asn-PABC-Mitomycin [7](260 mg, 0.35 Mmoles) in DMA/CH$_2$Cl$_2$ (⅔ mL) at Room temperature was treated with succinic anhydride (50 mg, 0.5 mmoles) and DIEA (130 mg, 1.0 mmoles). The reaction mixture was stirred overnight. To the above reaction mixture, ethyl ether (100 mL) was added and stirred for 30 minutes. The supernatant was removed and the process was repeated twice. The residue was triturated in 2% HOAc/ethyl acetate (50 mL) and the solid was collected by filtration, rinsed thoroughly with ethyl acetate and dried in vacuum to give a purple product (265 mg, 90% yield).
LC/MC: (M-H)$^-$=838

Example 9

Preparation of N$^\alpha$-acetamide-Ala-Ala-Asn-PABC-mitomycin [9]

Ala-Ala-Asn-PABC-mitomycin [7](37 mg, 0.05 mmoles) in DMA/CH$_2$Cl$_2$ (⅓ mL) at room temperature was treated with acetic anhydride (10 mg, 0.1 mmoles) and DIEA (13 mg, 0.1 mmoles). After 30 minutes, ethyl ether (50 mL) was added and stirred for 60 minutes. The soft solid was collected by filtration, rinsed with ethyl ethers and re-dissolved in methanol (5 mL). Solvent was removed under reduced pressure and the residue was triturated in 50% ethyl acetate/hexane (10 mL) and the solid was collected by filtration, rinsed thoroughly with ethyl acetate/hexane, dried in vacuum to give a purple product (35 mg, 90% yield).
LC/MC: (MH)$^+$=780; (M+Na)+=805

Example 10

Preparation of N$^\alpha$-butyramide-Ala-Ala-Asn-PABC-mitomycin [10]

Ala-Ala-Asn-PABC-mitomycin [7](37 mg, 0.05 mmoles) in DMA/CH$_2$Cl$_2$ (⅓ mL) at room temperature was treated with butyryl chloride (6.3 mg, 0.06 mmoles) and DIEA (13 mg, 0.1 mmoles). After 30 minutes, ethyl ether (50 mL) was added and stirred for 60 minutes. The solid was collected by filtration, rinsed with ethyl ethers and re-dissolved in methanol (5 mL). Solvent was removed under reduced pressure and the residue was triturated in ethyl acetate (10 mL). The solid was collected by filtration, rinsed thoroughly with ethyl acetate and dried in vacuum to give a purple product (27 mg, 67% yield).
LC/MC: (MH)$^+$=808; (M+Na)$^+$=833.

Example 11

Preparation of N$^\alpha$-hexanamide-Ala-Ala-Asn-PABC-mitomycin [11]

Ala-Ala-Asn-PABC-mitomycin [7](37 mg, 0.05 mmoles) in DMA/CH$_2$Cl$_2$ (⅓ mL) at room temperature was treated with hexaneoyl chloride (9.0 mg, 0.06 mmoles) and DIEA (13 mg, 0.1 mmoles). After 30 minutes, ethyl ether (50 mL) was added and stirred for 60 minutes. The solid was collected by filtration, rinsed with ethyl ethers and re-dissolved in methanol (5 mL). Solvent was removed under reduced pressure and the residue was triturated in 50% ethyl acetate/hexane (10 mL). The solid was collected by filtration, rinsed thoroughly with ethyl acetate and dried in vacuum to give a purple product (27 mg, 67% yield).

LC/MC: $(MH)^+=836$; $(M+Na)^+=860$

Example 12

Preparation of $N^\alpha$-[-(2-amide-2-oxoethoxy) acetic acid]-Ala-Ala-Asn-PABC-mitomycin [12]

Ala-Ala-Asn-PANC-mitomycin [7](295 mg, 0.4 mmoles) in THF/DMF (4/0.5 mL) was treated with 1,4-dioxane-2,6-dione (70 mg, 0.6 mmoles) and DIEA (60 mg, 0.5 mmoles) at room temperature for 2 hours. Ethyl ether (10 mL) was added slowly and the mixture was stirred for 30 min. Solvent was removed and the residue was triturated and sonicated in 1% acetic acid in ethyl acetate. Solid was collected by filtration, rinsed thoroughly with ethyl acetate and dried in vacuum to give a dark color product (276 mg, 80% yield).

LC/MC: $(M-H)^-=854$

Example 13

Preparation of $N^\alpha$-[-((2-amide-2-oxoethoxy) (methyl)amino) acetic acid]-Ala-Ala-Asn-PABC-mitomycin [13]

Ala-Ala-Asn-PANC-mitomycin [7](295 mg, 0.4 mmoles) in THF/DMF (4/0.5 mL) was treated with 4-methylmorpholine-2,6-dione (77 mg, 0.6 mmoles) and DIEA (130 mg, 1.0 mmole) at room temperature for 2 hours. Ethyl ether (10 mL) was added slowly and the mixture was stirred for 30 min. Solvent was removed and the residue was triturated and sonicated in 1% acetic acid in ethyl acetate. Solid was collected by filtration, rinsed thoroughly with ethyl acetate and dried in vacuum to give a dark color product (339 mg, 97% yield).

LC/MS: $(M-H)^-=867$

Example 14

Preparation of $N^\alpha$-Fmoc-Asn(N-trityl)-PAB-OH [14]

A solution of N-Fmoc-Asn(N-trityl) ((1.49 g, 2.5 mmoles), p-aminobenzyl alcohol (0.37 g, 3.0 mmoles) and EEDQ (0.74 g, 3 mmoles) in THF (50 mL) were stirred at room temperature overnight. Additional amount of EEDQ (0.25 g, 1.0 mmole) was added and stirred for another 6 hours. Reaction solution was diluted with ethyl acetate (300 mL) washed with 0.1 N HCl three times and dried over $Na_2SO_4$. The acetate solution was filtered through a short silica plug, rinsed with ethyl acetate and concentrated to dryness. The residue was triturated in ethyl ether, filtered, rinsed with ethyl ether and dried in vacuum to give a white solid (1.65 g, 93% yield).

LC/MS: $(MH)^+=702$

Example 15

Preparation of Asn(N-trityl)-PAB-OH [15]

To a solution of $N^\alpha$-Fmoc-Asn(N-trityl)-PAB-OH [14] (1.6 g, 2.28 mmoles) in $CH_2Cl_2$ (50 mL) was added DBU (1 mL). The reaction solution was stirred for 15 min. The reaction solution was diluted with $CH_2Cl_2$ (200 mL), washed with brine twice and dried over $Na_2SO_4$, filtered and concentrated to dryness. The residue was triturated in hexane/ethyl ether (1/1). Solid was collected by filtration, rinsed with ethyl ether and dried in vacuum to give a white product (1.1 g, 100% yield).

LC/MS: $(MH)^+=480$

Example 16

Preparation of $N^\alpha$-Fmoc-Ala-Ala-Asn (N-trityl)-PAB-OH [16]

A solution of Asn(N-trityl)-PAB-OH [15](0.72 g, 1.5 mmoles), $N^\alpha$-Fmoc-Ala-Ala [1](0.57 g, 1.5 mmol), PyBop (0.94 g, 1.8 mmoles) and DIEA (1.17 g, 9.0 mmoles) in NMP (20 mL) was stirred at room temperature for 1 hour. To the above reaction, 5% citric acid aqueous solution (150 mL) was added slowly at ice-water temperature and stirred for 2 hours. The precipitate was collected by filtration and rinsed with 5% citric acid solution, followed by de-salt water. Solid was re-suspended in aqueous $NaHCO_3$ solution, triturated, filtered, rinsed with de-salt water and dried in vacuum over KOH to give a white product (1.1 g, 87% yield).

LC/MS: $(MH)^+=845$

Example 17

Preparation of $N^\alpha$-Fmoc-Ala-Ala-Asn(N-trityl)-PABC-PNP[17]

A reaction solution of $N^\alpha$-Fmoc-Ala-Ala-Asn(N-trityl)-PAB-OH [16](1.1 g, 1.3 mmol), p-nitrophenyl chloroforrnate (0.31 g, 1.6 mmoles) and pyridine (0.13 g, 1.6 mmoles) in dry THF was stirred at room temperature overnight. Additional amount of p-nitrophenyl chloroforrnate (0.2 g, 1.0 mmole) and pyridine (0.08 g, 1.0 mmole) were added and stirred for another 4 hours. The above solution was diluted with ethyl acetate (300 mL) and washed with 5% citric acid solution (3×100 mL), followed by brine, dried over $Na_2SO_4$, filtered and concentrated to dryness.

Residue was triturated in ethyl ether, filtered, rinsed with ethyl ether and dried in vacuum to give an off-white product (1.1 g, 83% yield).

LC/MS: $(MH)^+=1010$

Example 18

Preparation of $N^\alpha$-Fmoc-Ala-Ala-Asn-PABC-PNP [18]

A solution of $N^\alpha$-Fmoc-Ala-Ala-Asn(N-trityl)-PABC-PNP[17](1.0 g, 1 mmole) and TIPS (2.5 mL) in TFA/$CH_2Cl_2$ (6/24 mL) was stirred at room temperature for 2 hours. To the above reaction solution, ethyl ether (150 mL) was added slowly and the suspension was stirred for 1 hour. Precipitate was collected by filtration and rinsed with ethyl ether. The solid was triturated in ethyl acetate, filtered, rinsed with ethyl acetate and dried in vacuum to give an off-white product (0.75 g, 97% yield).

LC/MS: $(MH)^+=767$

Example 19

Preparation of $N^\alpha$-Fmoc-Ala-Ala-Asn-PABC-doxorubicin[19]

A reaction solution of $N^\alpha$-Fmoc-Ala-Ala-Asn-PABC-PNP[18](383 mg, 0.5 mmoles), doxorubicin hydrochloride salt (348 mg, 0.6 mmoles), HOBT (202 mg, 1.5 mmoles) and DIEA (325 mg, 2.5 mmoles) in dry DMF (5 mL) was stirred in dark place overnight. To the above solution, 5% citric acid (100 mL) was added slowly at ice-water temperature and stirred for 1 hour. Precipitate was collected by filtration, rinsed with 5% citric acid, followed by de-salt water. The solid was re-suspended in aqueous $NaHCO_3$ solution and stirred for 30 min. Solid was collected, rinsed thoroughly with $NaHCO_3$ solution, followed by de-salt water. The solid was re-suspended in isopropanol, 10% methanol/ethyl acetate, triturated, filtered and dried in vacuum to give a dark red product (550 mg, 94% yield) LC/MS: $(MH)^+=1171$ Example 20

Preparation of Ala-Ala-Asn-PABC-doxorubicin [20]

A solution of $N^\alpha$-Fmoc-Ala-Ala-Asn-PABC-doxorubicin [19](500 mg, 0.42 mmoles) in 20% morpholine/NMP (5 mL) was stirred for 1 hour. To the above reaction solution, ethyl ether (50 mL) was added slowly and the resulted suspension was stirred for 30 min. The ethyl ether was poured off (repeated three times). The residue was triturated in ethyl acetate, 20% methanol/ethyl acetate. Solid was collected by filtration and dried in vacuum. The solid was re-suspended in water, sonicated, filtered and dried in vacuum over KOH to give a dark red product (320 mg, 80% yield).

LC/MC: $(MH)^+=949$

Similar methods for the preparation of Example 8, 12 and 13 were used for the preparation of Example of 21, 22 and 23 from compound [20].

Example 21

$N^\alpha$-succinamic acid-Ala-Ala-Asn-PABC-doxorubicin [21]

LC/MS: $(MH)^+=1049$

Example 22

$N^\alpha$-[-(2-amide-2-oxoethoxy) acetic acid]-Ala-Ala-Asn-PABC-doxorubicin [22]

LC/MS: $(MH)^+=1065$

Example 23

$N^\alpha$-[-((2-amide-2-oxoethoxy) (methyl)amino) acetic acid]-Ala-Ala-Asn-PABC-doxorubicin [23]

LC/MS: $(MH)^+=1078$

Example 24

Preparation $N^\alpha$-Fmoc-Asn-PABC-camptothecin[24]

To a suspension of camptothecin (348 mg, 1 mmole) and DAMP (366 mg, 3 mmoles) in dry $CH_2Cl_2$ (20 mL), triphosgene (100 mg, 0.33 mmoles) was added at ice-water temperature with stirring. After 20 min., a suspension of $N^\alpha$-Fmoc-Asn-PAB-OH [2](459 mg, 1 mmole) in dry $CH_2Cl_2$ (10 mL) was added to above reaction mixture and stirred overnight at room temperature. To the resulting reaction mixture, p-nitrophenyl chloroformate (100 mg, 0.5 mmoles) was added, followed by additional amount of DAMP (60 mg, 0.5 mmoles), and the reaction mixture was stirred for another 4 hours. After concentration, the resulting residue was triturated with 25% $CH_2Cl_2$/ethyl acetate, filtered, rinsed with 25% $CH_2Cl_2$/ethyl acetate and dried in vacuum. Solid was suspended in aqueous $NaHCO_3$, sonicated, filtered, rinsed thoroughly with aqueous $NaHCO_3$, followed by 5% citric acid, de-salt water and dried in vacuum over KOH to give a off-yellow product (763 mg, 91% yield).

LC/MS: (MH)=834

Example 25

Preparation of Asn-PABC-camptothecin[25]

A solution of $N^\alpha$-Fmoc-Asn-PABC-camptothecin[24] (500 mg, 0.6 mmoles) in 2% $DBU/CH_2Cl_2$ (15 mL) was stirred for 20 min. Ethyl ether (80 mL) was added slowly into above reaction solution and stirred for 30 min. Precipitate was triturated, collected by filtration and rinsed thoroughly with ethyl ether. Solid was re-triturated in 20% $CH_2Cl_2$/ethyl acetate, filtered and dried. The solid was re-suspended in aqueous $NaHCO_3$, triturated, filtered, rinsed with de-salt water and dried in vacuum over KOH to give an off-yellow product (295 mg, 80% yield).

LC/MS: (MH)=612

Example 26

Preparation of $N^\alpha$-Fmoc-Ala-Ala-Asn-PABC-camptothecin[26]

A solution of $H_2N$-Asn-PABC-camptothecin[25](244 mg, 0.4 mmoles), $N^\alpha$-Ala-Ala [1](190 mg, 0.5 mmoles), PyBop (260 mg, 0.5 mmoles) and DIEA (325 mg, 2.5 mmoles) in NMP (5 mL) was stirred for 1 hour. To the above reaction solution, 5% citric acid (50 mL) was added slowly and the resulted mixture was stirred for 30 min. Precipitate was collected by filtration, rinsed with 5% citric acid, followed by de-salt water and dried in vacuum over KOH. The solid was triturated in 15% $CH_2Cl2$/ethyl acetate, sonicated, filtered and dried to give a gray color product (274 mg, 70% yield).

LC/MS: $(MH)^+=976$

Example 27

Preparation of Ala-Ala-Asn-PABC-camptothecin[27]

A solution of $N^\alpha$-Fmoc-Ala-Ala-Asn-PABC-camptothecin[26](487 mg, 0.5 mmoles) in 2% $DBU/CH_2Cl_2$ (10 mL) was stirred for 10 min. To the above reaction solution, ethyl ether (50 mL) was added slowly and stirred for 30 min. Precipitate was collected, rinsed with ether. The solid was suspended in 20% $CH_2Cl_2$/ethyl acetate, triturated, filtered, rinsed with ethyl acetate and dried to give a gray color product (290 mg, 77% yield).

LC/MS: $(MH)^+=754$

Similar methods for the preparation of Example 8, 12 and 13 were used for the preparation of Example of 28, 29 and 30 from compound [27].

Example 28

N$^\alpha$-succinamic acid-Ala-Ala-Asn-PABC-camptothecin[28]

LC/MS: (MH)$^+$=854

Example 29

N$^\alpha$-[-(2-amide-2-oxoethoxy) acetic acid]-Ala-Ala-Asn-PABC-camptothecin [29]

LC/MS: (MH)$^+$=870

Example 30

N$^\alpha$-[-((2-amide-2-oxoethoxy) (methyl)amino) acetic acid]-Ala-Ala-Asn-PABC-camptothecin [30]

LC/MS: (MH)$^+$=883

Example 31

Preparation of N$^1$-Ala-Ala-Asn-PABC-mitomycin, N$^4$-Ala-Ala-Asn-PABC-doxorubicin-succinamide [31]

A solution of N$^\alpha$-succinamic acid-Ala-Ala-Asn-PABC-mitomycin [8](85 mg, 0.1 mmole), Ala-Ala-Asn-PABC-doxorubicin [20](104 mg, 0.1 mmoles), PyBop (62 mg, 0.12 mmoles) and DIEA (78 mg, 0.6 mmoles) in NMP (2 mL) was stirred for 1 hour. Ethyl ether (20 mL) was added and the resulted mixture was stirred and sonicated. The ether was poured off (repeated twice) and the residue was triturated in methanol, filtered and dried to give a dark color product (100 mg, 57% yield)

LC/MS: (MH)$^+$=1770

Example 32

Preparation of N$^1$-Ala-Ala-Asn-PABC-mitomycin, N-Ala-Ala-Asn-PABC-doxorubicin-bis(O$^\alpha$)-acetamide[32]

Similar methods for the preparation of Example 31 were used for the preparation of Example 32, from compound [20] and compound [12].

LC/MS: (MH)$^+$=1786

Example 33

Preparation of N$^1$-Ala-Ala-Asn-PABC-mitomycin, N-Ala-Ala-Asn-PABC-doxorubicin-bis(N$^\alpha$-methyl)-acetamide[33]

Similar methods for the preparation of Example 31 were used for the preparation of Example 33, from compound [20] and compound [13].

LC/MS: (MH)$^+$=1799

Example 34

Preparation of N$^1$-Ala-Ala-Asn-PABC-mitomycin, N$^4$-Ala-Ala-Asn-PABC-camptothecin-succinamide [34]

Similar methods for the preparation of Example 31 were used for the preparation of Example 34, from compound [27] and compound [8].

LC/MS: (MH)$^+$=1575

Example 35

Preparation of N$^1$-Ala-Ala-Asn-PABC-mitomycin, N$^5$-Ala-Ala-Asn-PABC-camptothecin-bis(O$^\alpha$)-acetamide[35]

Similar methods for the preparation of Example 31 were used for the preparation of Example 34, from compound [27] and compound [12].

LC/MS: (MH)$^+$=1591

Example 36

Preparation of N$^1$-Ala-Ala-Asn-PABC-mitomycin, N$^5$-Ala-Ala-Asn-PABC-camptothecin-bis(N$^\alpha$-methyl)-acetamide[36]

Similar methods for the preparation of Example 31 were used for the preparation of Example 34, from compound [27] and compound [13].

LC/MS: (MH)$^+$=1604

Abbreviations used in the examples:
DCC=dicyclohexylcarbodiimide
DCM=dichloromethane
DCU=dicyclohexylurea
DIEA=diisopropylethylamine
DMA=dimethylacetamide
DMEM=Dulbecco's modified Eagle medium
DMF=N,N-dimethylformamide
DMSO=dimethylsulfoxide
EDC=1-Ethyl-3-(3-dimethylaminopropyl)carbodiimide
EDTA=N,N',N'',N'''N''''-ethylenediaminetetraacetic acid
FBS=fetal bovine serum
Fmoc=fluorenylmethoxycarbamoyl
HATU=1-[Bis(dimethylamino)methylene]-1H-1,2,3-triazolo[4,5-b]pyridinium-3-oxid hexafluorophosphate
HOBT=N-Hydroxybenzotriazole
HPLC=high pressure liquid chromatography
IR=infrared spectroscopy
LC/MS=liquid chromatography/mass spectrometry
MS=mass spectrometry
MTD=maximum tolerated dose
NMP=N-methylpyrrolidinone
NMR=nuclear magnetic resonance
PABC=p-aminobenzylcarbamoyl
PBS=phosphate buffered saline
Py=pyridine
QW=per week
TCA=trichloroacetic acid
Tr=trityl, triphenylmethyl
UV/VIS=ultraviolet/visible spectroscopy

What is claimed is:

1. A peptide-drug conjugate, which is N$^\alpha$-succinamic acid-Ala-Ala-Asn-PABC-mitomycin; or a pharmaceutically acceptable salt thereof, wherein the mitomycin is bonded to PABC at a C-1" aziridine nitrogen of the mitomycin; and PABC is a p-aminobenzyl carbamoyl linker moiety.

2. A pharmaceutical composition comprising at least one peptide-drug conjugate of claim 1, or a pharmaceutically acceptable salt thereof, and at least one pharmaceutically-acceptable carrier.

3. The pharmaceutical composition of claim 2, packaged as one or more individual dosages.

4. A method of treating cancer in a mammal in need thereof, wherein the method comprises administering an anti-cancer effective amount of a peptide-drug conjugate of claim 1, or a pharmaceutically acceptable salt thereof.

5. A method of treating cancer in a mammal in need thereof, wherein the method comprises administering an anti-cancer effective amount of a pharmaceutical composition of claim 2.

6. The method of claim 4, wherein said cancer is a solid tumor.

7. The method of claim 4, wherein said cancer is colon cancer, bladder cancer, breast cancer, cervical cancer, ovarian cancer, stomach cancer, pancreatic cancer, lung cancer, liver cancer, oesophageal cancer, bowel cancer, skin cancer, or prostate cancer.

8. The method of claim 4, wherein said cancer is colon cancer.

9. The method of claim 4, wherein said cancer is bladder cancer.

10. The method of claim 4, wherein said cancer is breast cancer.

11. The method of claim 4, wherein said cancer is cervical cancer.

12. The method of claim 4, wherein said cancer is ovarian cancer.

13. The method of claim 4, wherein said cancer is stomach cancer.

14. The method of claim 4, wherein said cancer is pancreatic cancer.

15. The method of claim 4, wherein said cancer is lung cancer.

16. The method of claim 4, wherein said cancer is liver cancer.

17. The method of claim 4, wherein said cancer is oesophageal cancer.

18. The method of claim 4, wherein said cancer is bowel cancer.

19. The method of claim 4, wherein said cancer is skin cancer.

20. The method of claim 4, wherein said cancer is prostate cancer.

* * * * *

UNITED STATES PATENT AND TRADEMARK OFFICE
CERTIFICATE OF CORRECTION

PATENT NO. : 9,579,317 B2  
APPLICATION NO. : 14/726897  
DATED : February 28, 2017  
INVENTOR(S) : Shaosong Chu Page 1 of 1

It is certified that error appears in the above-identified patent and that said Letters Patent is hereby corrected as shown below:

On the Title Page

Item (57), Column 2, Abstract, Line 2, delete "p-aminobenzolyl" and insert -- p-aminobenzyl --.

In the Claims

Column 36, Line 61, Claim 1, delete the text "moiety." and insert the following text:
-- moiety having the formula:

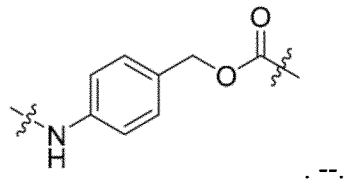

. --.

Signed and Sealed this  
Twelfth Day of March, 2019

Andrei Iancu  
*Director of the United States Patent and Trademark Office*